(12) United States Patent
Adachi et al.

(10) Patent No.: US 10,228,328 B2
(45) Date of Patent: Mar. 12, 2019

(54) ORGANIC ELECTRO-LUMINESCENT ELEMENT AND BIOINSTRUMENTATION DEVICE

(71) Applicants: Kyushu University, National University Corporation, Fukuoka-shi, Fukuoka (JP); HAMAMATSU PHOTONICS K.K., Hamamatsu-shi, Shizuoka (JP)

(72) Inventors: Chihaya Adachi, Fukuoka (JP); Hajime Nakanotani, Fukuoka (JP); Takahiko Yamanaka, Hamamatsu (JP); Shigeo Hara, Hamamatsu (JP); Toru Hirohata, Hamamatsu (JP)

(73) Assignees: Kyushu University, National University Corporation, Fukuoka-shi, Fukuoka (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/823,599

(22) Filed: Nov. 28, 2017

(65) Prior Publication Data
US 2018/0149595 A1     May 31, 2018

(30) Foreign Application Priority Data
Nov. 30, 2016    (JP) .................................. 2016-233234

(51) Int. Cl.
*G01N 21/64*    (2006.01)
*H01L 51/00*    (2006.01)
(Continued)

(52) U.S. Cl.
CPC ......... *G01N 21/6486* (2013.01); *H01L 27/15* (2013.01); *H01L 51/0034* (2013.01);
(Continued)

(58) Field of Classification Search
CPC . G01N 21/6486; H01L 27/15; H01L 51/0034; A61B 5/0059
(Continued)

(56) References Cited

U.S. PATENT DOCUMENTS

2016/0190478 A1    6/2016  Nakanotani et al.
2016/0372688 A1*  12/2016  Seo ..................... H01L 51/0085
(Continued)

FOREIGN PATENT DOCUMENTS

| JP | 5669163 | 12/2014 |
|----|---------|---------|
| JP | 2018-093175 | 6/2018 |

OTHER PUBLICATIONS

SOEI Statement of Related Matters identifying the U.S. Patent Publication No. US2018/0151810A1, Jul. 27, 2018, 1 page.
(Continued)

*Primary Examiner* — Nicole M Ippolito
(74) *Attorney, Agent, or Firm* — Soei Patent & Law Firm

(57) ABSTRACT

An organic EL element having a luminescence peak in a near-infrared range comprises a positive electrode, a negative electrode, and at least one organic layer including a luminescent layer located between the positive electrode and the negative electrode. The luminescent layer comprises a host material, a delayed fluorescent material and a luminescent material. The LUMO and HOMO energy levels of the delayed fluorescent material and the luminescent material, the absorption spectrum of the luminescent material, and the emission spectrum of the delayed fluorescent material satisfy predetermined relationships.

20 Claims, 7 Drawing Sheets

(51) Int. Cl.
 H01L 27/15 (2006.01)
 H01L 51/50 (2006.01)
 A61B 5/00 (2006.01)
(52) U.S. Cl.
 CPC ...... H01L 51/5004 (2013.01); H01L 51/5012 (2013.01); *A61B 5/0059* (2013.01); *H01L 51/0059* (2013.01); *H01L 51/0067* (2013.01); *H01L 51/0072* (2013.01); *H01L 2251/552* (2013.01)
(58) Field of Classification Search
 USPC ........................................... 250/493.1
 See application file for complete search history.

(56) References Cited

U.S. PATENT DOCUMENTS

2017/0123268 A1* 5/2017 Sasaki ............... G02F 1/133553
2017/0324055 A1* 11/2017 Ishisone ............. H01L 51/5028
2018/0151810 A1 5/2018 Adachi et al.

OTHER PUBLICATIONS

G. Qian et al., "Synthesis and Application of Thiadiazoloquinoxaline-Containing Chromophores as Dopants for Efficient Near-Infrared Organic Light-Emitting Diodes", J. Phys. Chem. C, 2009, p. 1589-p. 1595, vol. 113.

X. Du et al., "Efficient Non-doped Near Infrared Organic Light-Emitting Devices Based on Fluorophores with Aggregation-Induced Emission Enhancement", Chemistry of Materials, 2012, p. 2178-p. 2185, vol. 24.

G. Qian et al., "Simple and Efficient Near-Infrared Organic Chromophores for Light-Emitting Diodes with Single Electroluminescent Emission above 1000nm", Advanced Materials, 2009, p. 111-p. 116, vol. 21.

J. Mayerhoffer et al., "Synthesis and Molecular Properties of Acceptor-Substituted Squaraine Dyes", Chemistry a European Journal, 2013, p. 218-p. 232, vol. 19.

M. T. Sharbati et al., "Near-infrared electroluminescence from organic light emitting diode based on Imine oligomer with low turn on voltage", Optik, 2013, p. 52-p. 54, vol. 124.

X. Zhang et al., "Long-Wavelength, Photostable, Two-Photon Excitable BODIPY Fluorophores Readily Modifiable for Molecular Probes", The Journal of Organic Chemistry, 2013, p. 9153-p. 9160, vol. 78.

S. Wang et al., "Highly Efficient Near-Infrared Delayed Fluorescence Organic Light Emitting Diodes Using a Phenanthrene-Based Charge-Transfer Compound", Angewandte Chemie International Edition, 2015, p. 1-p. 6 vol. 54.

J. Lee et al., "Controlled emission colors and singlet-triplet energy gaps of dihydrophenazine-based thermally activated delayed fluorescence emitters", Journal of Materials Chemistry C, 2015, p. 2175-p. 2181, vol. 3.

Q. Zhang et al., "Anthraquinone-Based Intramolecular Charge-Transfer Compounds: Computational Molecular Design, Thermally Activated Delayed Fluorescence, and Highly Efficient Red Electroluminescence", Journal of the American Chemical Society, 2014, p. 18070-p. 18081, vol. 136.

H. Uoyama et al., "Highly efficient organic light-emitting diodes from delayed fluorescence", Nature, Dec. 13, 2012, p. 234-p. 238, vol. 492.

* cited by examiner

ORGANIC ELECTRO-LUMINESCENT ELEMENT AND BIOINSTRUMENTATION DEVICE

CROSS-REFERENCE TO RELATED APPLICATIONS

This application claims the benefit of priority from Japanese Patent Application No. 2016-233234, filed on Nov. 30, 2016, the entire contents of which are incorporated herein by reference. Additionally, this application includes related subject matter to U.S. patent application entitled "Organic Electro-Luminescent Element and Bioinstrumentation Device", filed on Nov. 28, 2017, which claims the benefit of priority from Japanese Patent Applications No. 2016-233256, filed on Nov. 30, 2016 and No. 2017-182853, filed on Sep. 22, 2017, the entire contents of which are incorporated herein by reference.

FIELD

An organic electro-luminescent element and bioinstrumentation device using the same.

BACKGROUND

Organisms contain a large number of substances, having absorption in every wavelength range. The near-infrared range, in the whole wavelength range, is hard to be absorbed by organisms compared to other wavelength ranges, so that biological sensing can be achieved by using the light in the near-infrared range. Specifically, biological sensing can be performed by a bioinstrumentation device including a near-infrared luminescent element and a photo detector, which are brought into close contact with an organic material, such as skin, for irradiating an organism with light, the detector detecting scattered light from the inside of the organism.

As conventional luminescent elements for use in such applications, solid-state elements based on inorganic semiconductors have been commonly used. Although devices using solid-state elements have been widely used in the field of bioinstrumentation, solid-state elements have problems such as poor biocompatibility in a broad sense including design freedom and flexibility.

In contrast, organic electro-luminescent elements (hereinafter also referred to as "organic EL element"), which recently attract attention, may be used as luminescent elements to possibly solve the problem. In other words, organic EL elements are excellent in processability and design freedom due to material properties and manufacturing process, and furthermore, flexibility may also be imparted to organic EL elements by deposition on a plastic substrate. As the organic EL elements that emit light in a near-infrared range, for example, those described in Non Patent Literature 1 to 6 are known.

CITATION LIST

[Patent Literature 1] JP5669163 B1
[Non Patent Literature 1] G. Qian et al. J. Phys. Chem. C 2009, 113, 1589-1595
[Non Patent Literature 2] X. Du et al. Chem. Mater. 2012, 24, 2178-2185
[Non Patent Literature 3] G. Qian et al. Adv. Mater. 2009, 21, 111-116
[Non Patent Literature 4] U. Mayerhoeffer et al. Chem. Eur. J. 2013, 19, 218-232
[Non Patent Literature 5] M. T. Sharbatia et al. Optik, 2013, 124, 52-54
[Non Patent Literature 6] X. Zhang et al. J. Org. Chem. 2013, 78, 9153-9160

SUMMARY

The organic EL elements described in Non Patent Literature 1 to 6, however, have room for improvement in the luminous efficiency thereof. Patent Literature 1 discloses that an organic EL element having a high luminous efficiency can be provided by using a delayed fluorescent material as assistant dopant, but, as a result of studies by the present inventors, it has been found difficult to manufacture organic EL elements that emit light in the near-infrared range applicable for use in bioinstrumentation based on the disclosure of Patent Literature 1. Furthermore, organic EL elements often have a plurality of maximal values of emission spectrum, and light emission in the visible light range (other than a near-infrared range) produces noise having a negative effect on the reliability of organism sensing, and is therefore undesirable.

An object of the present invention is, therefore, to provide an organic EL element that emits light in a near-infrared range, is excellent in both the electric properties and the device life, with a sufficiently low luminescent intensity of the maximal values in the emission spectrum in the visible light range, or with no maximal values observed in the visible light range, and a bioinstrumentation device using the same. The near-infrared range may generally be understood to include a lower limit of approximately 700 nm and an upper limit of approximately 2500 nm. By way of non-exhaustive example, some embodiments of the present invention may be configured to operate in a near-infrared range of approximately 700 nm to 800 nm, or near the maximum luminescence values. In still other example embodiments, the upper limit of the near-infrared range may be approximately 900 nm or approximately 1000 nm according to different example configurations.

The present invention includes an organic EL element having a luminescence peak in a near-infrared range, comprising a positive electrode, a negative electrode, and at least one organic layer including a luminescent layer located between the positive electrode and the negative electrode. The luminescent layer comprises a host material, a delayed fluorescent material and a luminescent material. The delayed fluorescent material and the luminescent material may satisfy the relationships (1) to (4) shown below:

$$\Delta HOMO + \Delta LUMO \leq 0.6 \text{ eV} \quad (1);$$

$$|\Delta HOMO| \leq 0.4 \text{ eV} \quad (2);$$

$$|\Delta LUMO| \leq 0.4 \text{ eV} \quad (3);$$

wherein "$\Delta HOMO$" represents a value of a highest occupied molecular orbital (HOMO) energy level of the luminescent material minus a HOMO energy level of the delayed fluorescent material, and "$\Delta LUMO$" represents a value of a lowest unoccupied molecular orbital (LUMO) energy level of the delayed fluorescent material minus a LUMO energy level of the luminescent material; and $$|P_{Abs} - P_{Em}| \leq 30 \text{ nm} \quad (4)$$

wherein $P_{Abs}$ represents a maximal value at the longest wavelength side of an absorption spectrum of the luminescent material, and $P_{Em}$ represents a maximal value at the longest wavelength side of an emission spectrum of the delayed fluorescent material.

Additionally, some example embodiments include a bioinstrumentation device comprising the organic EL element and a photo detector.

According to some example embodiments, a bioinstrumentation device may include an organic EL element that emits light in a near-infrared range from a wavelength of 700 nm or more, is excellent in both the electric properties and the device life, with a sufficiently low luminescent intensity of the maximal values in the emission spectrum in the visible light range, or with no maximal values observed in the visible light range.

DETAILED DESCRIPTION

Figure 1:
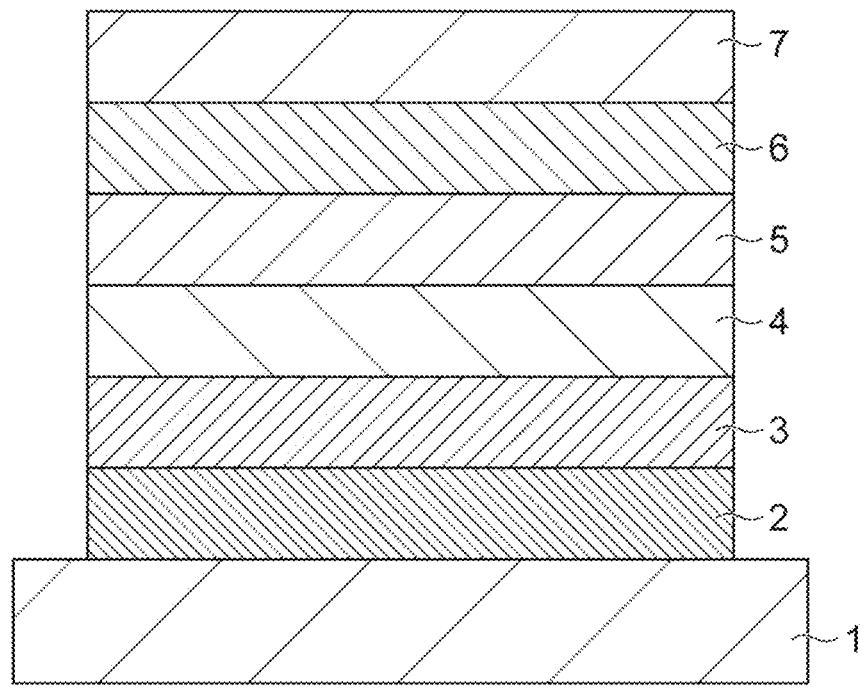
FIG. 1 is a schematic cross-sectional view showing a layer structure of an organic EL element.

Hereinafter, the present invention will be described in detail. Although the following constituent features will be described based on typical embodiments or specific examples of the present invention in some cases, the present invention is not limited to such embodiments or specific examples. A numerical range represented using "to" herein means a range containing the numerical values provided before and after the word "to" as the lower limit value and the upper limit value, respectively. The isotope species of hydrogen atoms present in the compound molecule for use in the present invention are not particularly limited. For example, all of the hydrogen atoms in the molecule may be $^1$H, or all or a part of the hydrogen atoms thereof may be $^2$H (deuterium D).

Herein, "host material" means an organic compound that confines at least the energy of a delayed fluorescent material in a luminescent layer; "delayed fluorescent material" means an organic compound that is capable of being transferred to the triplet excited state and then undergoing inverse intersystem crossing to the singlet excited state, and emits fluorescent light on returning from the singlet excited state to the ground state; and "luminescent material" means an organic compound that allows substantially no inverse intersystem crossing different from a delayed fluorescent material, but emits fluorescence when returned from the excited singlet state to the ground state.

Herein, the HOMO and LUMO of a delayed fluorescent material and a luminescent material, the absorption spectrum of a luminescent material, and the emission spectrum of a delayed fluorescent material are defined as ones which can be measured by the methods shown below.

(HOMO)

On an As-doped n-type bare Si wafer having a mirror-finished surface, a resistivity of 0.0030 to 0.0060 Ω·cm, and a crystal orientation <100>, a delayed fluorescent material or a luminescent material is deposited singly, and the HOMO level is measured by a photoelectron spectroscopic measurement apparatus AC-3E (manufactured by Riken Keiki Co., Ltd.) in the atmosphere. Although it is preferable in some example embodiments that the film thickness be 100 nm, the measurement is performed at a thickness of about 30 nm when the film is formed by spin coating, due to the difficulty in making a thick film.

(LUMO and Absorption Spectrum of Luminescent Material)

On a quartz substrate, a delayed fluorescent material or a luminescent material is deposited singly and the absorption spectrum is measured by a UV-VIS-NIR spectrophotometer LAMBDA 950 (manufactured by Perkin Elmer, Inc.). In this example, the film thickness is adjusted such that the absorption peak at the longest wavelength side has an optical density (OD) of 0.1 to 1.0. With regard to the luminescent material, $P_{Abs}$ is defined as the maximal absorption value at the longest wavelength side. With regard to the LUMO level, $\lambda_{edge}$ [nm] is defined as the wavelength at the intersection between the tangent line drawn along the trailing gradient at the long wavelength side of the longest wavelength-side peak of each of the obtained absorption spectra and the horizontal axis (wavelength axis), and the calculation is performed based on the formula 1 shown below, using the value of HOMO [eV] obtained by the method described above.

$$LUMO\ [eV] = HOMO + \left(\frac{1240}{\lambda_{edge}}\right) \quad \text{[Formula 1]}$$

The tangent line along the trailing gradient is drawn as follows. Moving along the spectrum curve from the long wavelength side to the maximal value of an absorption peak, tangent lines may be drawn on the respective points on the spectrum curve. The slope of the tangent lines increases as the curve rises (in other words, as the vertical axis increases). A tangent line drawn at a point showing the maximal value of the slope is defined as the tangent line along the trailing gradient on the long wavelength side of the absorption spectrum.

(Measurement of Emission Spectrum of Delayed Fluorescent Material)

On a quartz substrate, a host material and a delayed fluorescent material are deposited such that the mass ratio therebetween is the same as the ratio between the host material and the delayed fluorescent material in an organic EL element, and the emission spectrum is measured by a fluorescence spectrophotometer FLUOROMAX (manufactured by Horiba, Ltd.), then the maximal value at the longest wavelength side of the spectrum obtained in the present measurement is defined as $P_{Em}$. For example, when a luminescent layer is formed at a mass ratio of (host material):(delayed fluorescent material):(luminescent material)=79:20:1, the composition of the film for use in the present measurement is controlled to have a mass ratio of (host material):(delayed fluorescent material) is 79:20. As the conditions for measurement, in some example embodiments, it is preferable that the slit width at the upstream or the downstream be 10 nm or less, and the film thickness be 30 nm or more and 200 nm or less.

[Layer Structure of Organic EL Element]

The organic EL element of the present invention comprises a positive electrode, a negative electrode, and at least one organic layer including a luminescent layer located between the positive electrode and the negative electrode.

The organic layer may consist of a luminescent layer only, or may include one or more organic layers in addition to the luminescent layer. Examples of such other organic layers include a hole transport layer, a hole injection layer, an electron blocking layer, a hole blocking layer, an electron injection layer, an electron transport layer, and an exciton blocking layer. The hole transport layer may be a hole injection/transport layer having a hole injection function, and the electron transport layer may be an electron injection/transport layer having an electron injection function. An example structure of a specific organic EL element is shown in FIG. 1. In FIG. 1, a substrate 1, a positive electrode 2, a hole injection layer 3, a hole transport layer 4, a luminescent layer 5, an electron transport layer 6, and a negative electrode 7 are shown.

Hereinafter, each of the components and each of the layers of an organic EL element will be described.

[Luminescent Layer]

The luminescent layer is a layer that emits light after the formation of excitons by recombination of holes and electrons injected from a positive electrode and a negative electrode, respectively. In some example embodiments of the organic EL element, the luminescent layer comprises a host material, a delayed fluorescent material and a luminescent material, and the delayed fluorescent material and the luminescent material satisfy the relationships (1) to (4) shown below:

$$\Delta HOMO + \Delta LUMO \leq 0.6 \text{ eV} \quad (1);$$

$$|\Delta HOMO| \leq 0.4 \text{ eV} \quad (2);$$

$$|\Delta LUMO| \leq 0.4 \text{ eV} \quad (3)$$

wherein "ΔHOMO" represents a value of a HOMO energy level of the luminescent material minus a HOMO energy level of the delayed fluorescent material, and "ΔLUMO" represents a value of a LUMO energy level of the delayed fluorescent material minus a LUMO energy level of the luminescent material; and $$|P_{Abs} - P_{Em}| \leq 30 \text{ nm} \quad (4)$$

wherein $P_{Abs}$ represents a maximal value at the longest wavelength side of an absorption spectrum of the luminescent material, and $P_{Em}$ represents a maximal value at the longest wavelength side of an emission spectrum of the delayed fluorescent material.

From the viewpoint of improving the electric characteristics and the device life of an organic EL element, it is preferable in some example embodiments that ΔHOMO+ΔLUMO in the relationship (1) be 0.5 eV or less, and in other example embodiments more preferably 0.4 eV or less.

From the viewpoint of improving the electric characteristics and the device life of an organic EL element, it is preferable in some example embodiments that each of the absolute values of ΔHOMO and ΔLUMO in the relationships (2) and (3) be 0.3 eV or less.

From the viewpoint of improving the electric characteristics and the device life of an organic EL element, it is preferable in some example embodiments that the absolute value of $P_{Abs} - P_{Em}$ in the relationship (4) be 25 nm or less, 20 nm or less, or 15 nm or less. In some example embodiments, a smaller absolute value of $P_{Abs} - P_{Em}$ may be more preferable.

(Host Material)

The host material is an organic compound that confines at least the energy of a delayed fluorescent material in a luminescent layer, and may further have at least a function for transporting carriers (electrons and/or holes) in the luminescent layer. In some example embodiments, it is preferable that the host material have a larger minimum excited triplet energy at 77 K than the delayed fluorescent material. The host materials may be used singly or in combinations of two or more thereof.

In some example embodiments, it is preferable that the host material be an organic compound that has a hole transport capability and an electron transport capability, prevents wavelength elongation of the emitted light, and also has a high glass transition temperature. Examples of preferred compounds which can be used as host material are shown below. In the structural formulas of the following example compounds, R and $R_1$ to $R_{10}$ each independently represent a hydrogen atom or a substituent; and n represents an integer of 3 to 5.

[Chemical Formula 1]

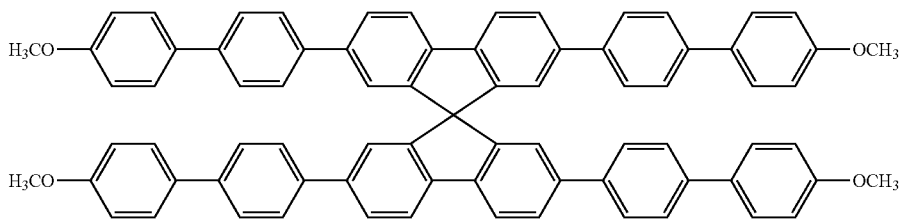

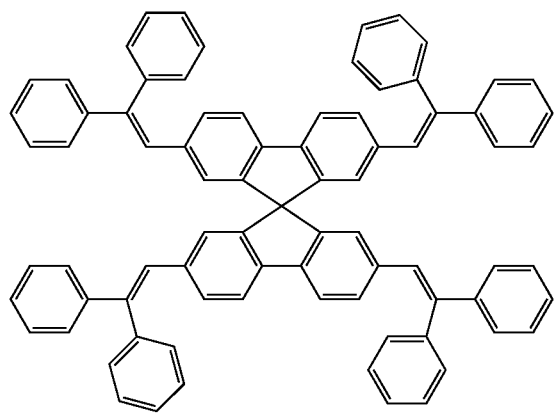
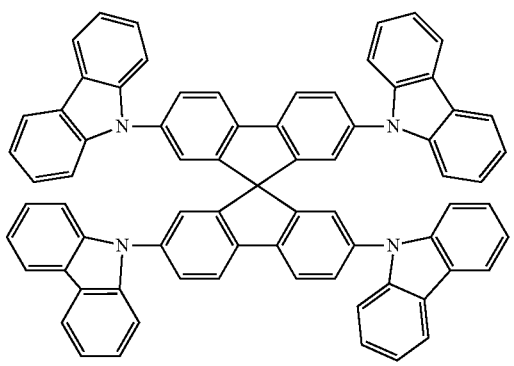
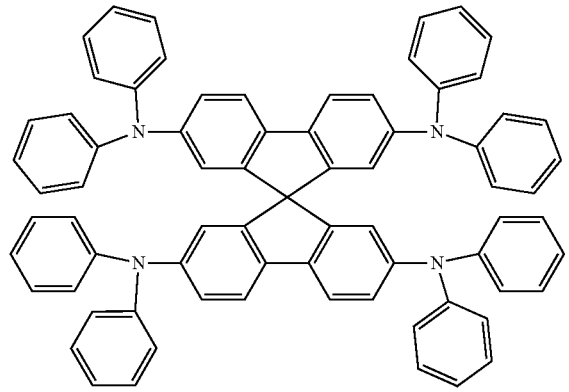
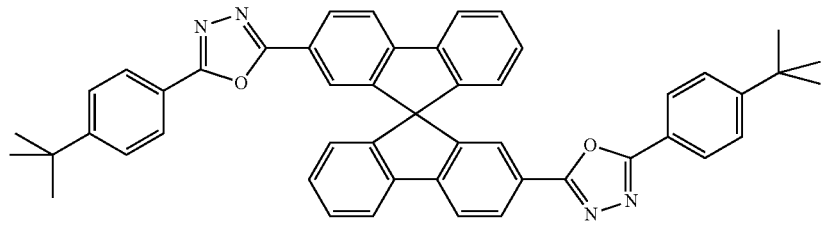
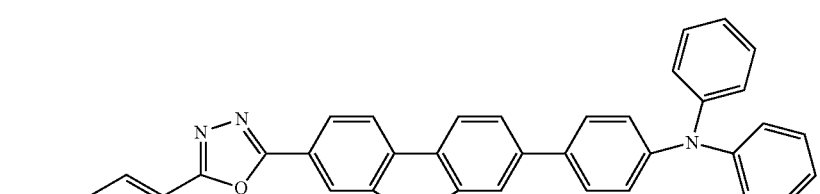
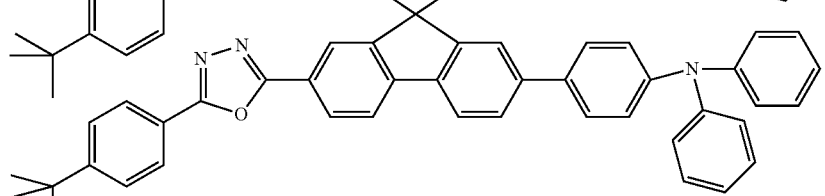
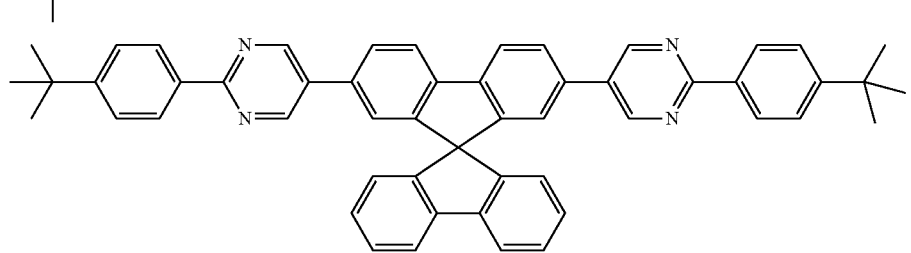

[Chemical Formula 2]
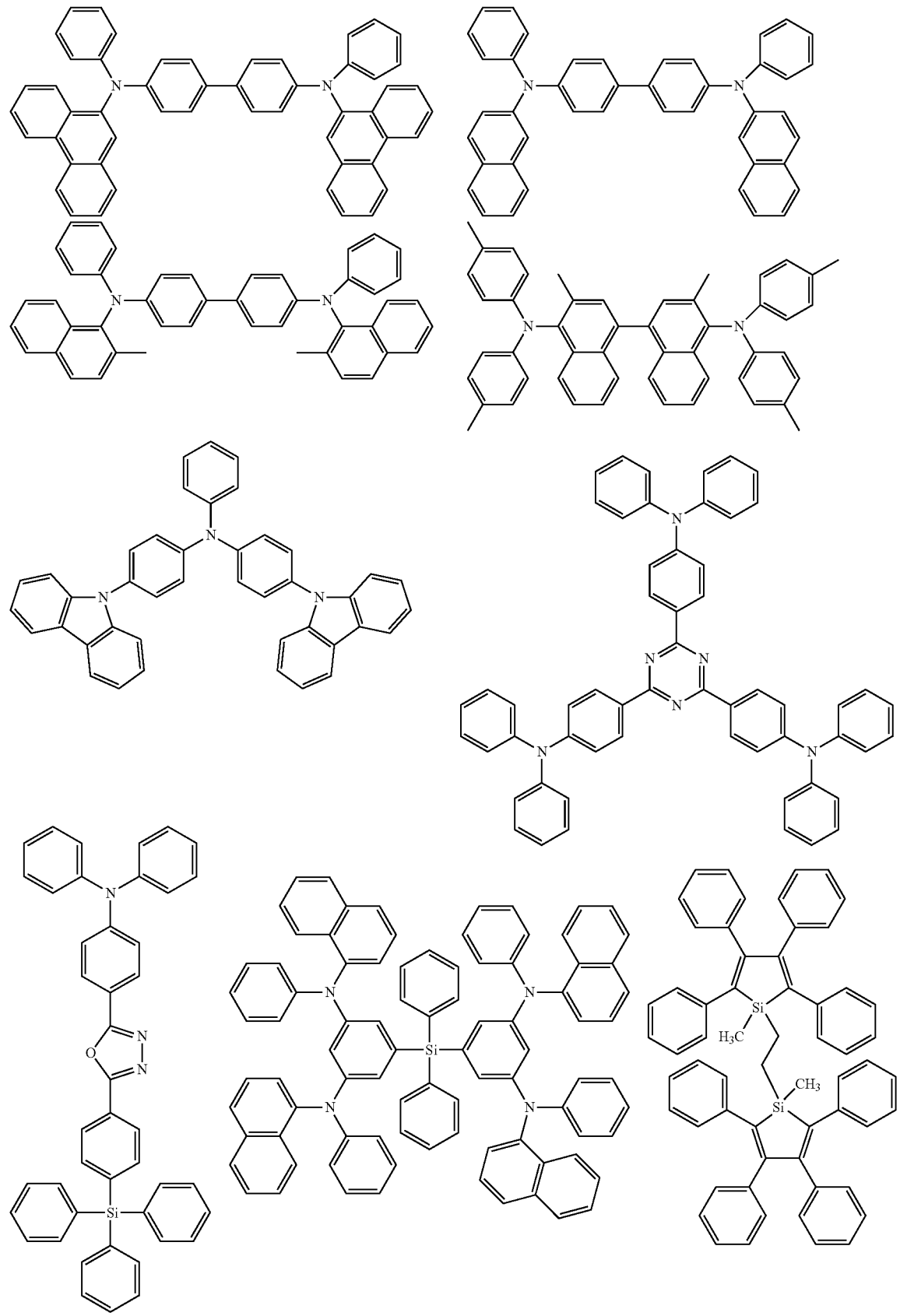

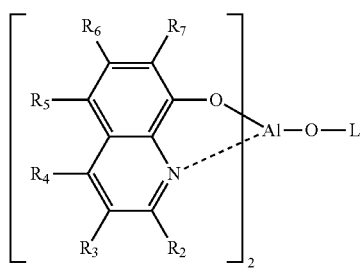
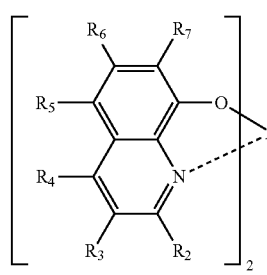
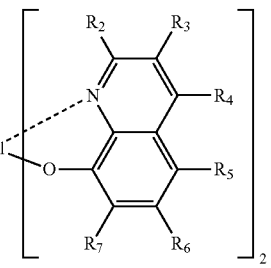
[Chemical Formula 3]
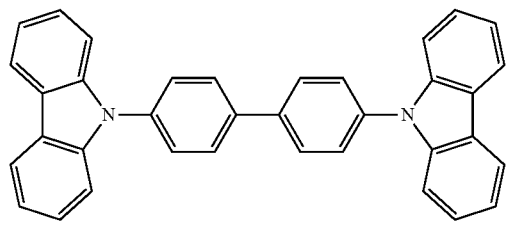
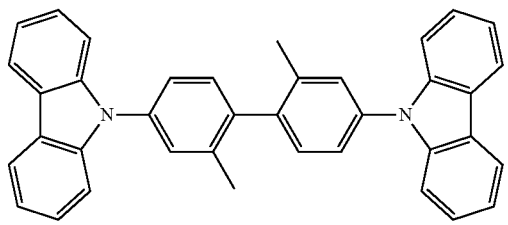
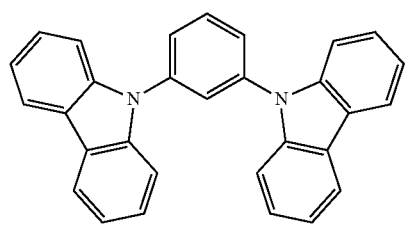
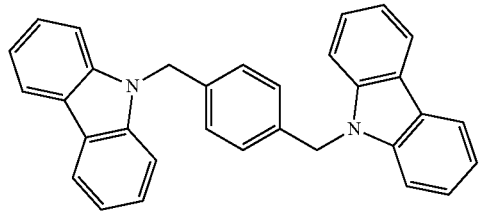
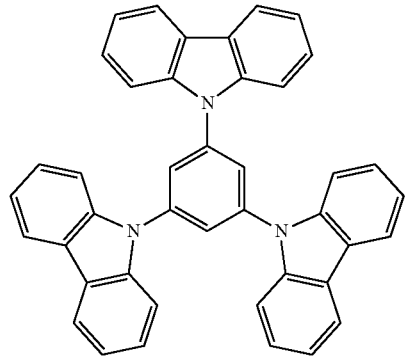
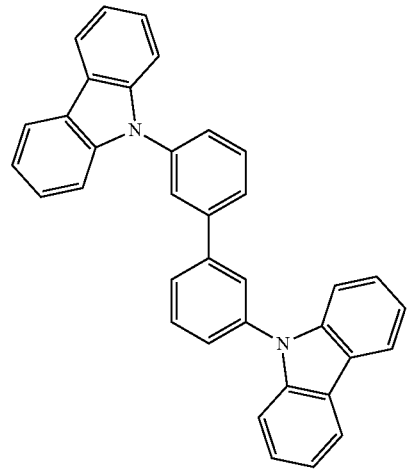
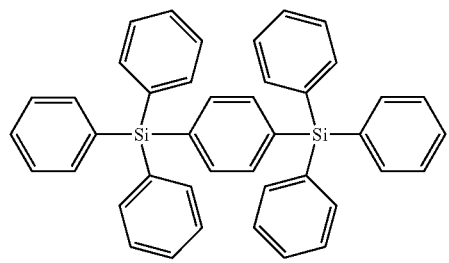
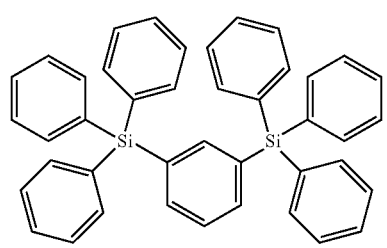

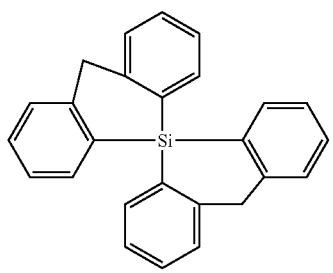
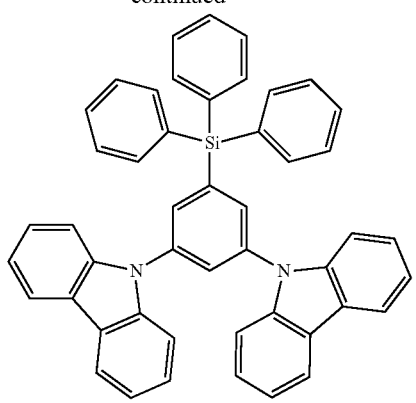
[Chemical Formula 4]
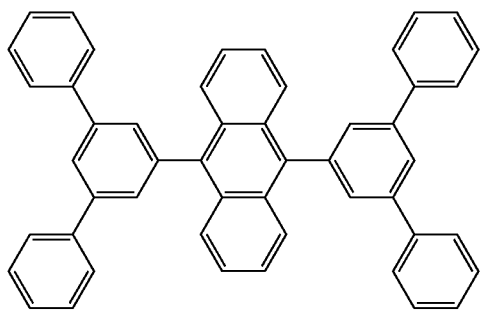
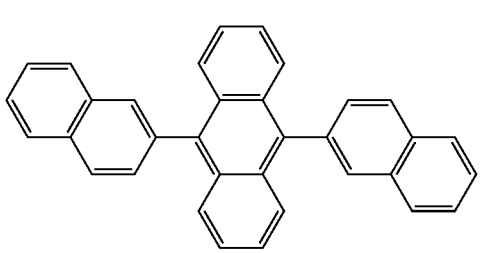
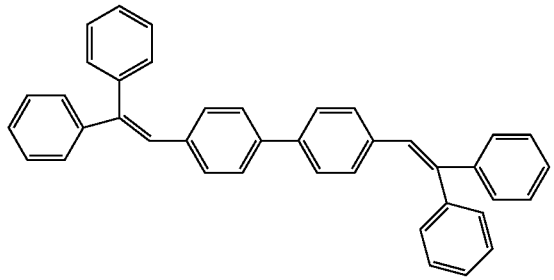
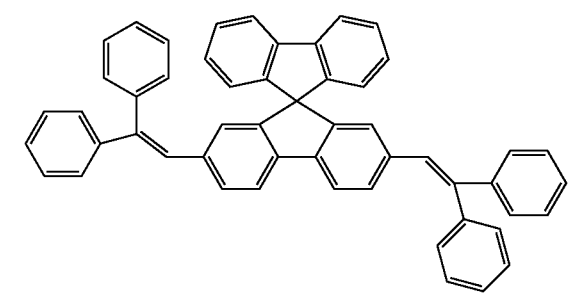
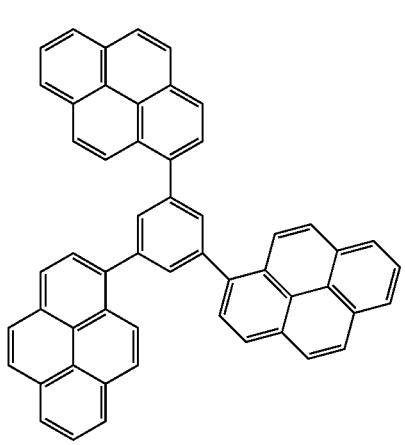
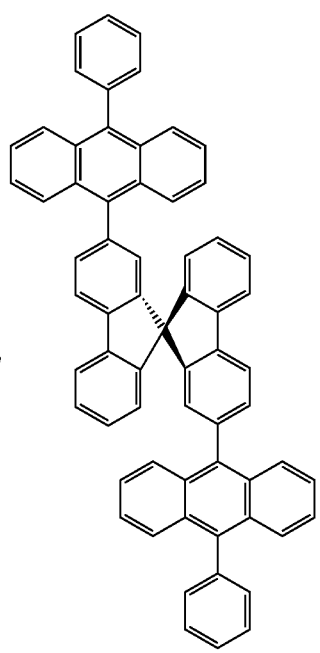
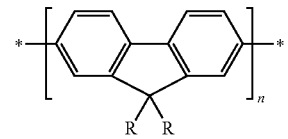

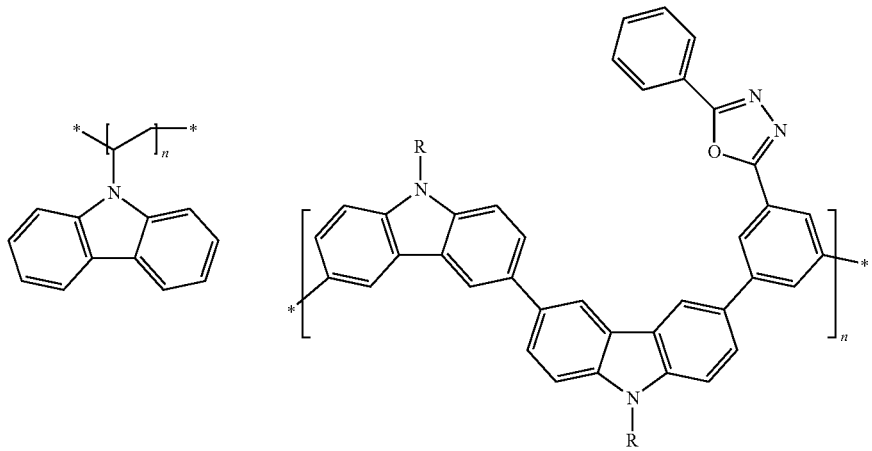

[Chemical Formula 5]

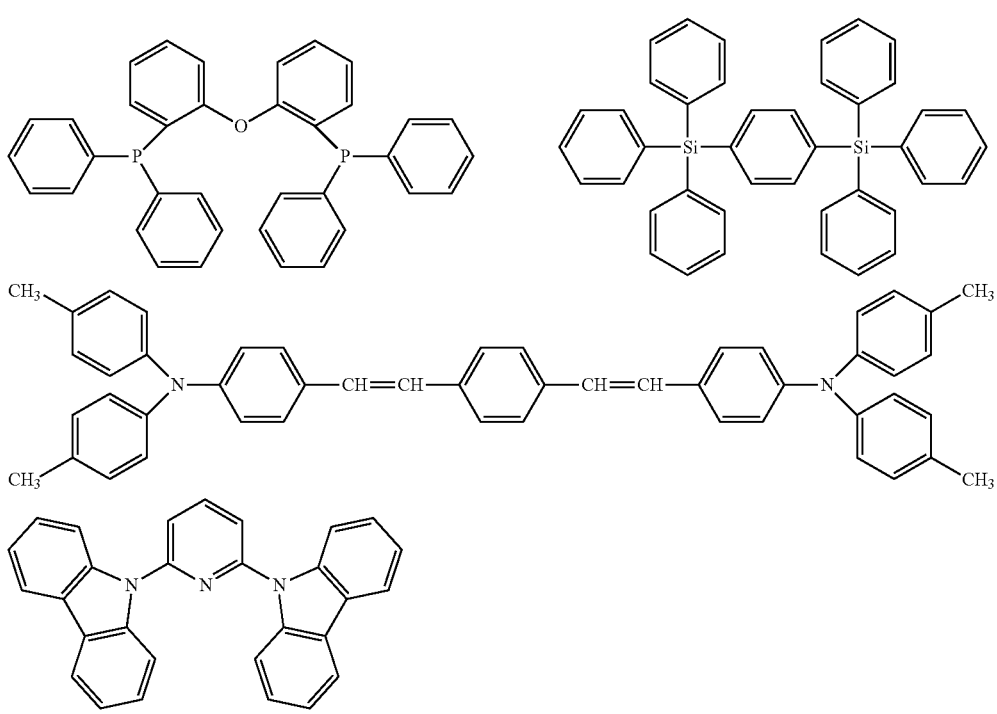

(Delayed Fluorescent Material)

In some example embodiments, it is preferable that the delayed fluorescent material be a thermally activated delayed fluorescent material that allows reverse intersystem crossing from an excited triplet state to an excited singlet state by absorption of thermal energy. The thermally activated delayed fluorescent material relatively easily allows reverse intersystem crossing from an excited triplet state to an excited singlet state by absorbing heat generated by a device and thus allows the excited triplet energy to efficiently contribute to light emission. In some example embodiments, it is preferable that the delayed fluorescent material be an organic compound that has a smaller minimum excited singlet energy than the host material and has a larger minimum excited singlet energy than the luminescent material.

The delayed fluorescent material has a difference $\Delta E_{st}$ between the energy level $E_{s1}$ in the minimum excited singlet state and the energy level $E_{T1}$ in the minimum excited triplet state at 77 K of 0.3 eV or less, 0.2 eV or less, 0.1 eV or less, and 0.08 eV or less. In some example embodiments, a lower difference $\Delta E_{st}$ may be preferable. With an energy difference $\Delta E_{st}$ in the range of approximately 0.3 eV or less, the delayed fluorescent material relatively easily allows reverse intersystem crossing from an excited triplet state to an excited singlet state, allowing the excited triplet energy to efficiently contribute to light emission.

In some example embodiments, it is preferable that a delayed fluorescent material that emits light in a normal red to deep red to near-infrared range when used as dopant be selected as the delayed fluorescent material. Specific examples thereof include the compounds shown below.

[Chemical Formula 6]

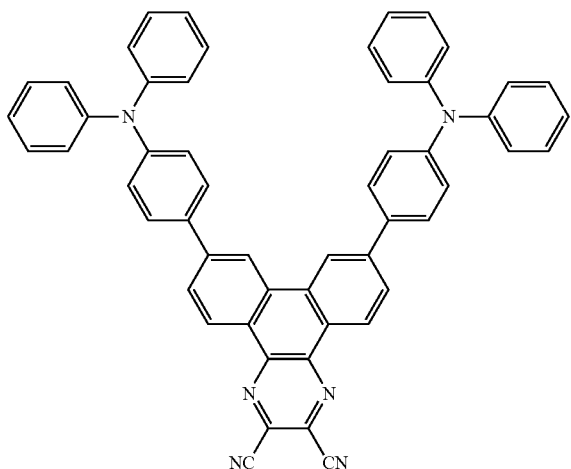

[Chemical Formula 7]

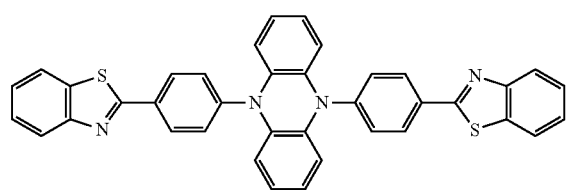

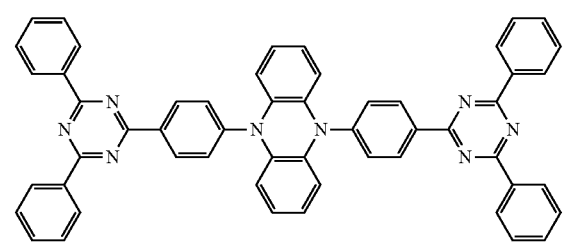

[Chemical Formula 8]

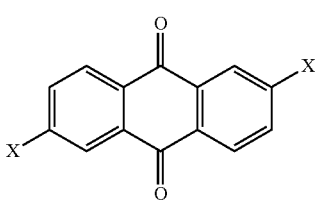

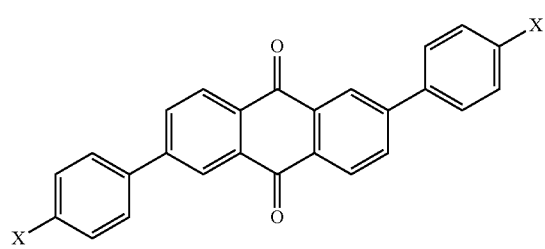

X =

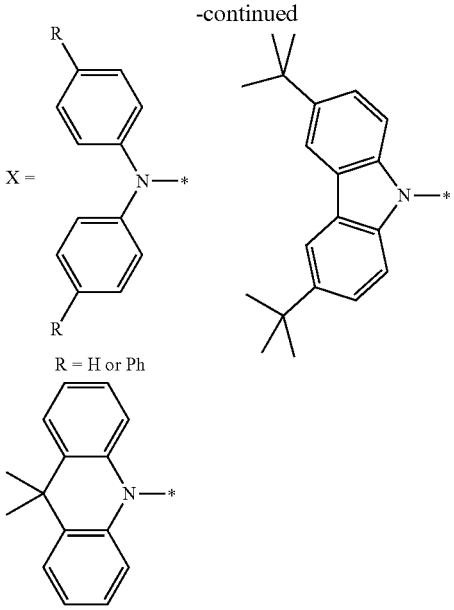

R = H or Ph

[Chemical Formula 9]

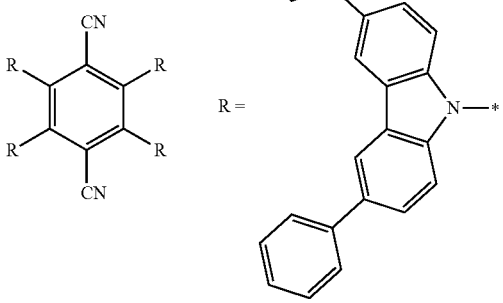

These compounds may be produced by, for example, the methods described in the following literatures.

S. Wang et al. Angew. Chem. Int. ed. 2015, 54, 1-6
J. Lee et al. J. Mater. Chem. C, 2015, 3, 2175-2181
Q. Zhang et al. J. Am. Chem. Soc. 2014, 136, 18070-18081
H. Uoyama et al. Nature 2012, 492, 234-238

(Luminescent Material)

The luminescent material receives energy from the host material in the excited singlet state and the delayed fluorescent material, and the delayed fluorescent material in the excited singlet state reached from the excited triplet state through reverse intersystem crossing so as to transition to the singlet excited state, and emits fluorescence when returned to the ground state thereafter. The luminescent material is not particularly limited as long as it can receive energy from the host material and the delayed fluorescent material so as to emit light, and the emitted light may be fluorescence or delayed fluorescence. In some example embodiments, it is preferable that $P_{ABS}$ of the luminescent material (maximal value at the longest wavelength side of absorption spectrum) be 500 to 1000 nm.

In some example embodiments, it is preferable that a luminescent material having a luminescence peak in a normal near-infrared range when used as dopant be selected as the luminescent material. Specific examples thereof include the compounds shown below.

[Chemical Formula 10]
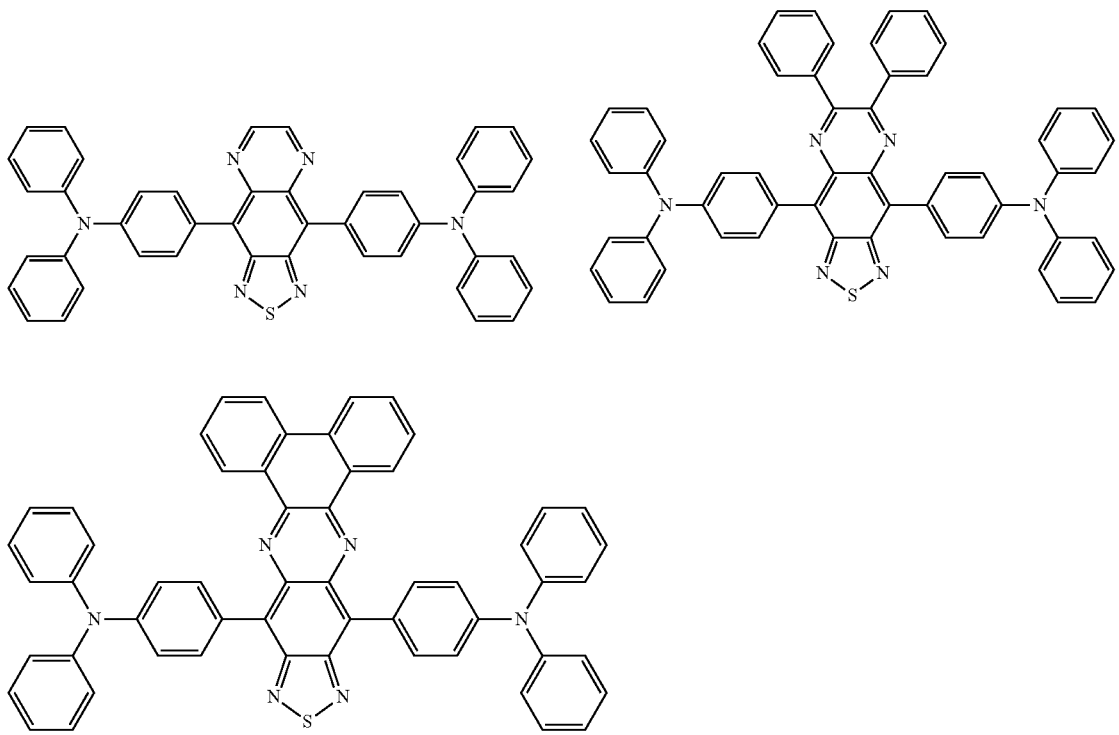
[Chemical Formula 11]
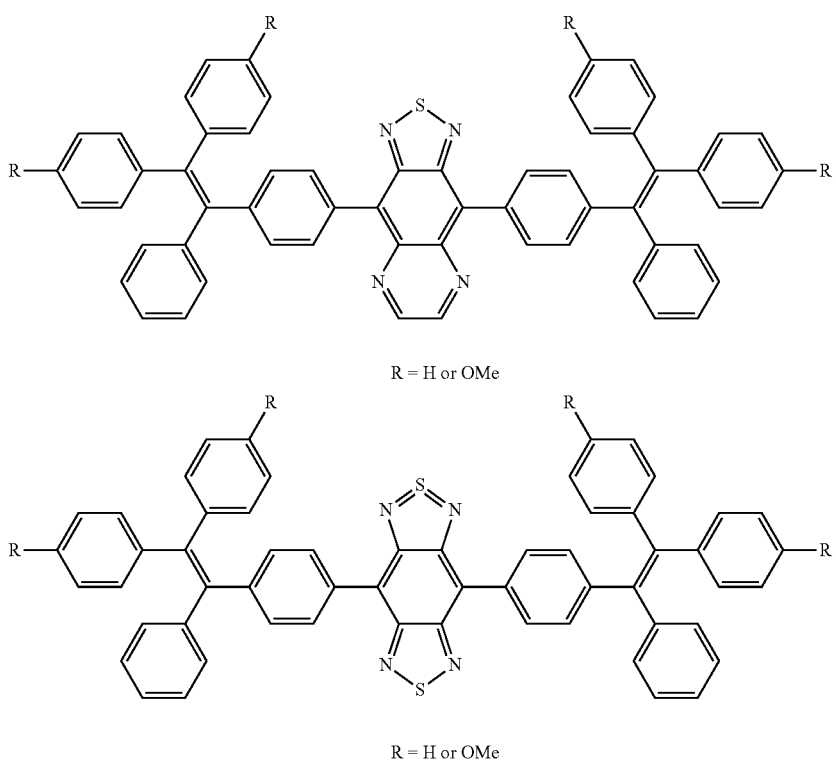
R = H or OMe
R = H or OMe -continued
[Chemical Formula 12]
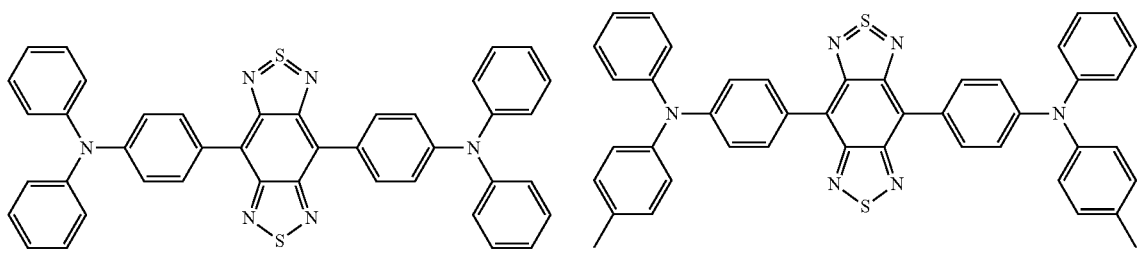
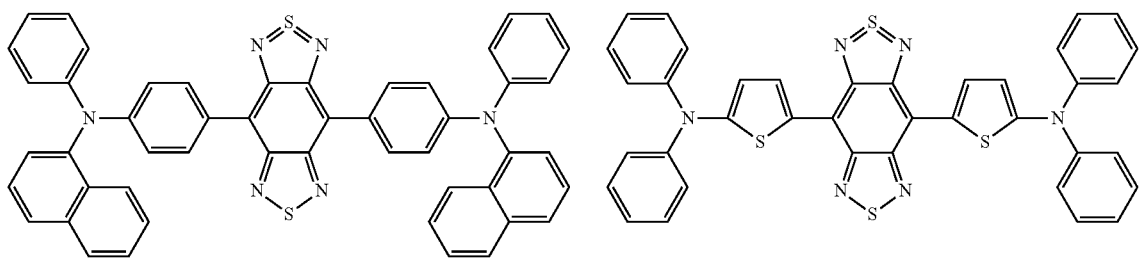
[Chemical Formula 13]
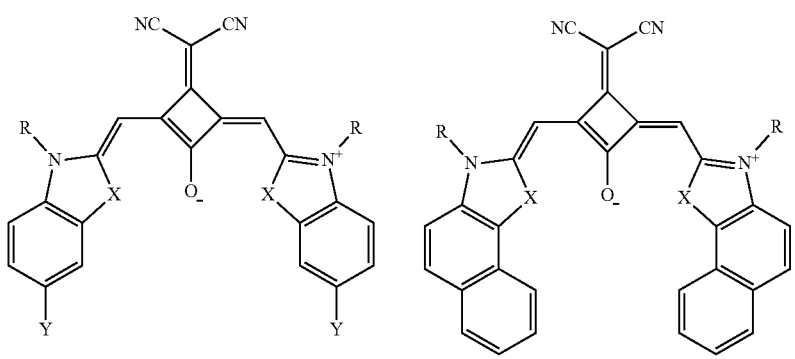
X = O; Y = H; R = C$_4$H$_9$
X = CMe$_2$; Y = H; R = C$_4$H$_9$
X = CMe$_2$; Y = F; R = C$_4$H$_9$
X = CMe$_2$; Y = Cl; R = C$_4$H$_9$
X = CMe$_2$; Y = Br; R = C$_4$H$_9$
X = CMe$_2$; Y = I; R = C$_4$H$_9$
X = S; Y = H; R = C$_4$H$_9$
X = S; Y = I; R = C$_4$H$_9$
X = Se; Y = H; R = C$_{12}$H$_{25}$
X = CH=CH; Y = H; R = C$_4$H$_9$
X = CMe; R = C$_4$H$_9$
X = S; R = C$_{12}$H$_{25}$
X = CH=CH; R = C$_{10}$H$_{21}$
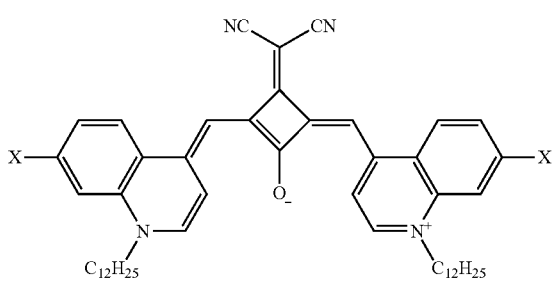
X = H
X = Cl
X = Br
X = I

[Chemical Formula 14]

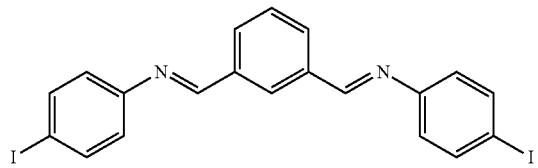

[Chemical Formula 15]

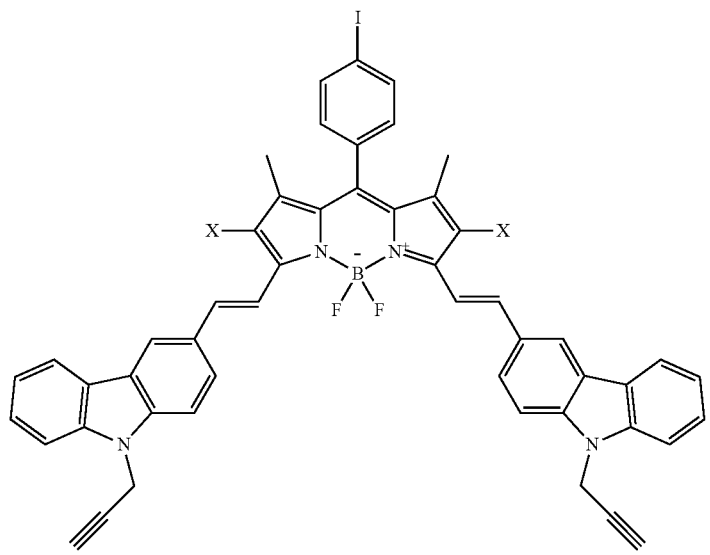

X = H
X = Cl

These compounds may be produced by, for example, the methods described in the following literatures.

G. Qian et al. J. Phys. Chem. C 2009, 113, 1589-1595
X. Du et al. Chem. Mater. 2012, 24, 2178-2185
G. Qian et al. Adv. Mater. 2009, 21, 111-116
U. Mayerhoeffer et al. Chem. Eur. J. 2013, 19, 218-232
M. T. Sharbatia et al. Optik, 2013, 124, 52-54
X. Zhang et al. J. Org. Chem. 2013, 78, 9153-9160

In some example embodiments, each of the delayed fluorescent material and the luminescent material may have a N-containing structure with two or three benzene rings bonded to an N atom, wherein two of the benzene rings are optionally bonded to each other to form a fused ring.

In the N-containing structure with two or three benzene rings bonded to an N atom, the two benzene rings may be bonded through, for example, a single bond, a carbon atom, an oxygen atom, a sulfur atom, or a nitrogen atom so as to form a fused ring. In the case of bonding through a carbon atom, the carbon atom may have one or two substituents, or may form a carbonyl group together with an oxygen atom. Specific examples of the fused ring that can be formed include the structures (2) to (6) shown below.

In some example embodiments, it is preferable that the N-containing structure described above be a structure selected from the structures (1) to (6) shown below. In other example embodiments, it is more preferable that the N-containing structure be the structure (1) or (2), or the structure (1). And in still example embodiments, it is more preferable that the N-containing structure be the structure (7).

[Chemical Formula 16]

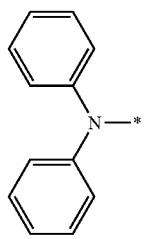
(1)

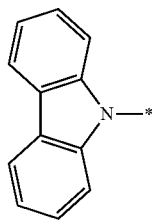
(2)

(3)

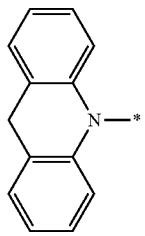

(4)

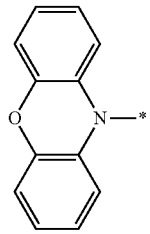

(5)

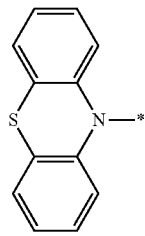

(6)

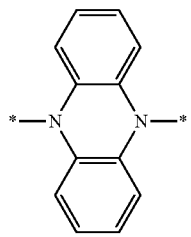

[Chemical Formula 17]

(7)

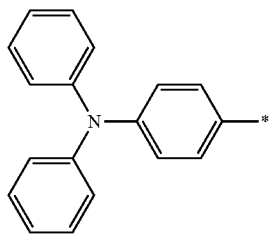

Although the benzene ring may further form a fused ring such as a naphthalene ring together with another aromatic ring or heterocycle, in some example embodiments it is preferable that the benzene ring not form a fused ring.

In some embodiments, the structure (1) to (7) may have one or more substituents. The examples of the substituents include alkyl groups having 1 to 6 carbon atoms, aryl groups having 6 to 10 carbon atoms and cyano groups.

In some example embodiments, it is preferable that each of the delayed fluorescent material and the luminescent material further have a fused ring in addition to the N-containing structure described above, and the fused ring structure of the delayed fluorescent material and the luminescent material each comprise an equivalent set of at least two successive rings, i.e. the fused rings of the delayed fluores-cent material and the luminescent material having a common structure of at least two successive rings. Examples of such structures include the structures shown below.

[Chemical Formula 18]

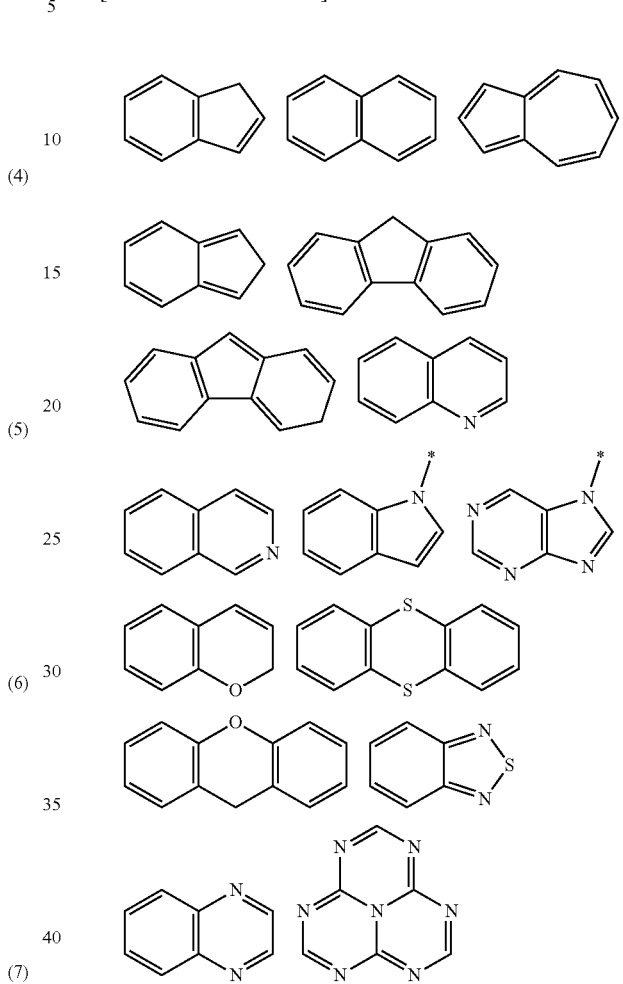

Regarding the structures in the fused rings, the apparent position of the double bonds in the chemical formulas are not necessarily the same because the double bonds are delocalized in the fused rings. For example, when comparing the two successive rings encircled by the broken lines in the following formulas (A) and (B), the position of the double bonds is different; however, the two successive rings in the formula (A) are equivalent to those in the formula (B). Specifically, the fused ring represented by formula (B) can also be represented by the following formula (B').

[Chemical Formula 19]

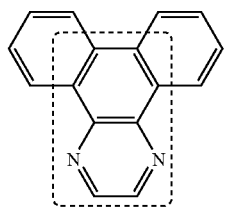

(A)

(B)

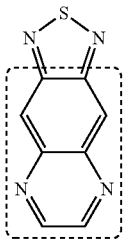

(B')

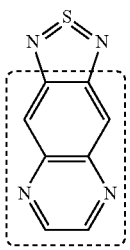

In some example embodiments, it is also preferable that each of the delayed fluorescent material and the luminescent material further has a common heterocycle (preferably an aromatic heterocycle) or a cyano group, in addition to the N-containing structures described above. Examples of the heterocycles include the structures shown below. These heterocycles may further form a fused ring together with another benzene ring or heterocycle.

[Chemical Formula 20]

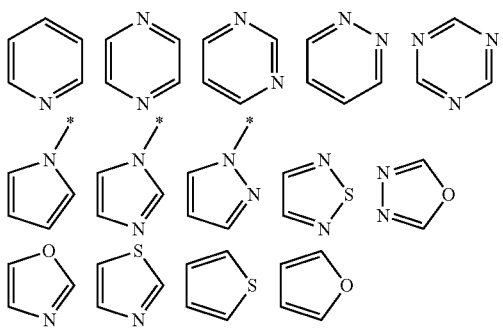

(Content of Host Material, Delayed Fluorescent Material and Luminescent Material)

Although the content of each organic compound contained in the luminescent layer is not particularly limited, it is preferable that the contents of the delayed fluorescent material and the luminescent material each be smaller than the content of the host material. As a result, a higher luminous efficiency can be achieved. Specifically, when the total weight of the host material content W1, the delayed fluorescent material content W2, and the luminescent material content W3 is assumed to be 100 wt %, the host material content W1 is preferably 15 wt % to 99.9 wt %, 50 wt % to 90 wt %, or 70 wt % to 80 wt %, the delayed fluorescent material content W2 is preferably 5.0 wt % to 50 wt %, 5.0 wt % to 45 wt %, or 10 wt % to 40 wt %, and the luminescent material content W3 is preferably 0.1 wt % to 5.0 wt %, 0.3 wt % to 4.0 wt %, or 0.5 wt % to 3.0 wt %.

(Other Organic Compounds)

The luminescent layer may include the host material, the delayed fluorescent material and the luminescent material only, or may include organic compounds in addition to those. Examples of such organic compounds include organic compounds having carrier (electron and/or hole) transport capability. As the organic compounds having hole transport capability and the organic compounds having electron transport capability, the following hole transport materials and electron transport materials may be referred to, respectively.

[Substrate]

In some example embodiments, it is preferable that the organic EL element of the present invention be supported by a substrate. Any substrate that is conventionally used for organic EL elements may be used without particular limitation, and, for example, a substrate made of glass, transparent plastic, quartz, or silicon may be used.

[Positive Electrode]

A positive electrode of an organic EL element that includes electrode material made of metal, alloy, electrically conductive compound, or mixture thereof having a large work function (4 eV or more) is preferably used. Specific examples of such electrode materials include metals such as Au, and transparent conductive materials such as, CuI, indium tin oxide (ITO), $SnO_2$, and ZnO. Alternatively, amorphous material such as IZO ($In_2O_3$—ZnO) from which a transparent conductive film can be made may be used. In preparation of the positive electrode, a thin film formed from those electrode materials by a method such as deposition or sputtering may be subjected to photolithography to form a pattern with a desired shape, alternatively in the case of not needing a precise pattern (about 100 μm or more), the pattern may be formed through a mask with a desired shape when the electrode material is deposited or sputtered. Alternatively, in the case of using an applicable material such as an organic conductive material, a wet deposition method such as printing and coating may also be used. In the case of producing light from the positive electrode, it is desirable that the transmittance be controlled to be higher than 10%, and it is preferable that the sheet resistance as positive electrode be several hundred Wsq. or less. Furthermore, the film thickness is selected usually from a range of 10 to 1000 nm, preferably from a range of 10 to 200 nm, depending on its material.

[Negative Electrode]

On the other hand, the negative electrode that includes electrode material made of metal (referred to as electron injecting metal), alloy, electrically conductive compound, or mixture thereof having a small work function (4 eV or less) is used. Specific examples of such electrode materials include sodium, sodium-potassium alloy, magnesium, lithium, magnesium/copper mixture, magnesium/silver mixture, magnesium/aluminum mixture, magnesium/indium mixture, aluminum/aluminum oxide ($Al_2O_3$) mixture, indium, lithium/aluminum mixture, and rare earth metals. Among them, in view of electron injection properties as well as durability against oxidation and the like, a mixture of an electron injecting metal and a stable second metal having a larger work function than the electron injecting metal is preferred, including magnesium/silver mixture, magnesium/aluminum mixture, magnesium/indium mixture, aluminum/aluminum oxide ($Al_2O_3$) mixture, lithium/aluminum mixture, and aluminum. The negative electrode can be manufactured by forming a thin film from these electrode materials by a method such as deposition or sputtering. In some example embodiments, it is preferable that the sheet resistance as negative electrode be several hundred Ω/sq. or less, and the film thickness is selected, usually from a range of 10 nm to 5 μm, preferably from a range of 50 to 200 nm. Also, in order to transmit the emitted light, it is convenient that any one of the positive electrode and the negative electrode of the organic EL element be transparent or translucent for improvement in luminance.

Furthermore, the transparent conductive materials given as examples in the section of positive electrode may be used to manufacture a transparent or translucent negative electrode, and by applying them, an element with both of the positive electrode and the negative electrode having transparency can be manufactured.

[Injection Layer]

The injection layer is a layer disposed between the electrode and the organic layer for reduction in driving voltage and improvement in luminance, including a hole injection layer and an electron injection layer, which may be present between the positive electrode and the luminescent layer or the hole transport layer, and between the negative electrode and the luminescent layer or the electron transport layer. The injection layer may be disposed on an as needed basis.

[Blocking Layer]

The blocking layer is a layer that can block the diffusion of electric charges (electrons or holes) and/or excitons present in the luminescent layer to the outside of the luminescent layer. The electron blocking layer can be disposed between the luminescent layer and the hole transport layer so as to block the electrons from passing through the luminescent layer toward the hole transport layer. In the same manner, the hole blocking layer can be disposed between the luminescent layer and the electron transport layer so as to block the holes from passing through the luminescent layer toward the electron transport layer. The blocking layer can also be used to block the excitons from diffusing to the outside of the luminescent layer. In other words, each of the electron blocking layer and the hole blocking layer may double as the exciton blocking layer. The electron blocking layer or exciton blocking layer herein means a layer having both functions of the electron blocking layer and the exciton blocking layer in itself.

[Hole Blocking Layer]

The hole blocking layer in a broad sense has the function of an electron transport layer. The hole blocking layer has roles for transporting electrons while blocking holes from reaching the electron transport layer, so that the probability of recombination of electrons and holes in the luminescent layer can be improved.

[Electron Blocking Layer]

The electron blocking layer in a broad sense has the function for transporting holes. The electron blocking layer has roles for transporting holes while blocking electrons from reaching the hole transport layer, so that the probability of recombination of electrons and holes in the luminescent layer can be improved.

[Exciton Blocking Layer]

The exciton blocking layer is a layer for blocking the exciton generated by the recombination of the holes and electrons in the luminescent layer from diffusing into the charge transport layer, of which insertion allows the excitons to be efficiently confined in the luminescent layer to thereby improve the luminous efficiency of an element. The exciton blocking layer may be inserted adjacent to the luminescent layer, on any of the positive electrode-side and the negative electrode-side, and insertion on both sides at one time is also possible. In other words, when having the exciton blocking layer on the positive electrode-side, the layer may be inserted between the hole transport layer and the luminescent layer, adjacent to the luminescent layer; and when inserted on the negative electrode-side, the layer may be inserted between the luminescent layer and the negative electrode, adjacent to the luminescent layer. Also, between the positive electrode and the exciton blocking layer adjacent to the luminescent layer on the positive electrode-side, the hole injection layer, the electron blocking layer, and the like may be included; and between the negative electrode and the exciton blocking layer adjacent to the luminescent layer on the negative electrode-side, the electron injection layer, the electron transport layer, the hole blocking layer, and the like may be included. When a blocking layer is disposed, it is preferable that at least any one of the excited singlet energy and the excited triplet energy of the material for use as blocking layer be higher than the excited singlet energy and the excited triplet energy of the luminescent material.

[Hole Transport Layer]

The hole transport layer is made of hole transport material having a function for transporting holes, and can be disposed as a single layer or multi layers.

The hole transport material has any of hole injection or transport properties and electron barrier properties, and may be any of an organic material and an inorganic material. Examples of the hole transport material for use include a triazole derivative, an oxadiazole derivative, an imidazole derivative, a carbazole derivative, an indolocarbazole derivative, a polyarylalkan derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer, and an electrically conductive polymer/oligomer, a thiophene oligomer in particular; while in some example embodiments, it is preferable to use a porphyrin compound, an aromatic tertiary amine compound, and a styrylamine compound, and in still other example embodiments it is more preferable to use an aromatic tertiary amine compound.

[Electron Transport Layer]

The electron transport layer is made of material having a function for transporting electrons, and can be disposed as a single layer or multi layers.

The electron transport material (which doubles as hole blocking material in some cases) has only to satisfy the function for transmitting electrons injected from the negative electrode to the luminescent layer. Examples of the electron transport layer for use include a nitro-substituted fluorene derivative, a diphenylquinone derivative, a thiopyrandioxide derivative, carbodiimide, a fluorenylidene methane derivative, anthraquinodimethane and anthrone derivatives, and an oxadiazole derivative. Furthermore, a thiadiazole derivative obtained by substituting the oxygen atom of the oxadiazole ring of the oxadiazole derivative with a sulfur atom, and a quinoxaline derivative having a quinoxaline ring known as electron-withdrawing group can also be used as the electron transport material. Furthermore, polymer materials having a polymer chain in which these materials are introduced or having a main chain of these materials can also be used.

The deposition method of these layers is not particularly limited, and any of a dry process and a wet process can be employed. For these layers, conventionally known organic compounds such as the compounds described in Patent Literature 1 can be used. Each of the films may include one organic compound only or two or more organic compounds.

Additionally, some example embodiments include an organic EL element including a positive electrode, a negative electrode, and at least one organic layer including a luminescent layer located between the positive electrode and the negative electrode, the luminescent layer comprising a host material, a delayed fluorescent material and a luminescent material. the EL elements may have a maximum luminescence in a near-infrared range with a wavelength of 700 nm or more, with no maximum luminescence being observed in a visible light range with a wavelength of less than 700 nm.

Although the number of the maximum luminescences in the near-infrared range in the organic EL element of the present invention may be one or more, in some example embodiments it is preferable that the number be one. Some luminescence peaks have a so-called shoulder, which is regarded as a maximum luminescence only when having a differentiated value of less than 0, and is not regarded as a maximum luminescence when having a differentiated value of 0 or more. For example, the EL spectrum in Example 1 has a shoulder near a wavelength of 650 nm, which is not a maximum luminescence.

The organic EL element having the constituents described above emits light when an electric field is applied between the positive electrode and the negative electrode. According to the organic EL element of the present invention, fluorescence emission due to the excited singlet energy is the main luminescence.

The organic EL element of the present invention can be applied to any of a single element, an element having array structure, and a structure having positive electrode and negative electrode disposed in an X-Y matrix form. The organic EL element of the present invention emits light in a near-infrared range, being applicable as, for example, a light source for optical communication, a light source for biometrics, and a light source for sensors, other than the bioinstrumentation devices described above.

[Bioinstrumentation Device]

The bioinstrumentation device comprises the organic EL element described above and a photo detector. According to the present device, an organism is exposed to the light in a near-infrared range from the organic EL element as light source for the measurement of the change in the intensity of optical absorption, reflected light, scattered light, and luminescence caused by the biological tissues, so that biological sensing can be performed.

EXAMPLES

Hereinafter, the present invention will be specifically described with reference to Examples, but the present invention is not limited to these Examples. In Examples and Comparative Examples, the relations between abbreviations and formulas are as follows.

[Chemical Formula 21]

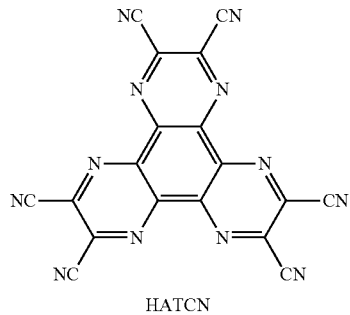

HATCN

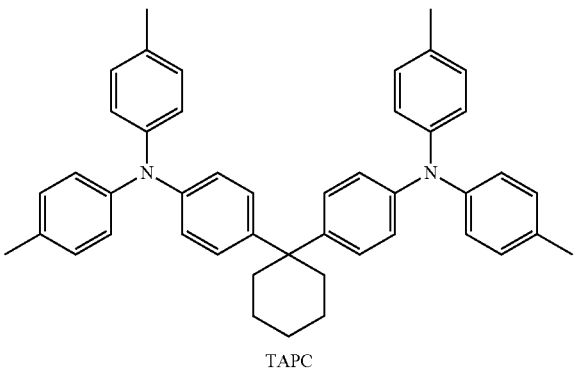

TAPC

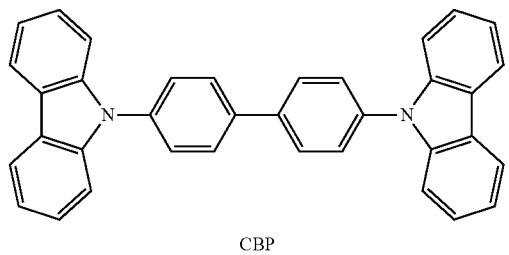

CBP

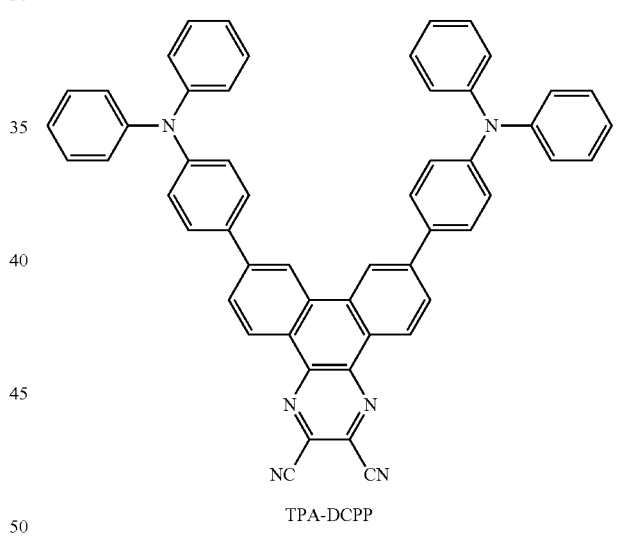

TPA-DCPP

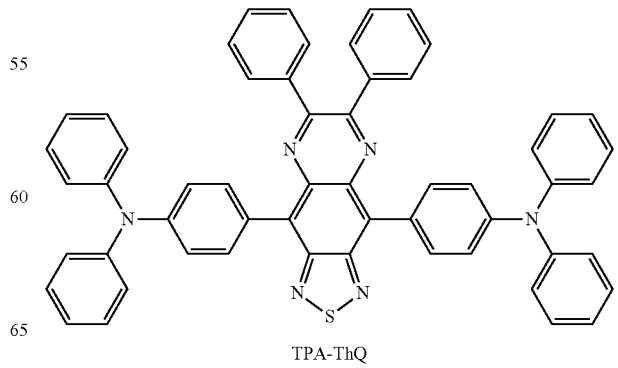

TPA-ThQ

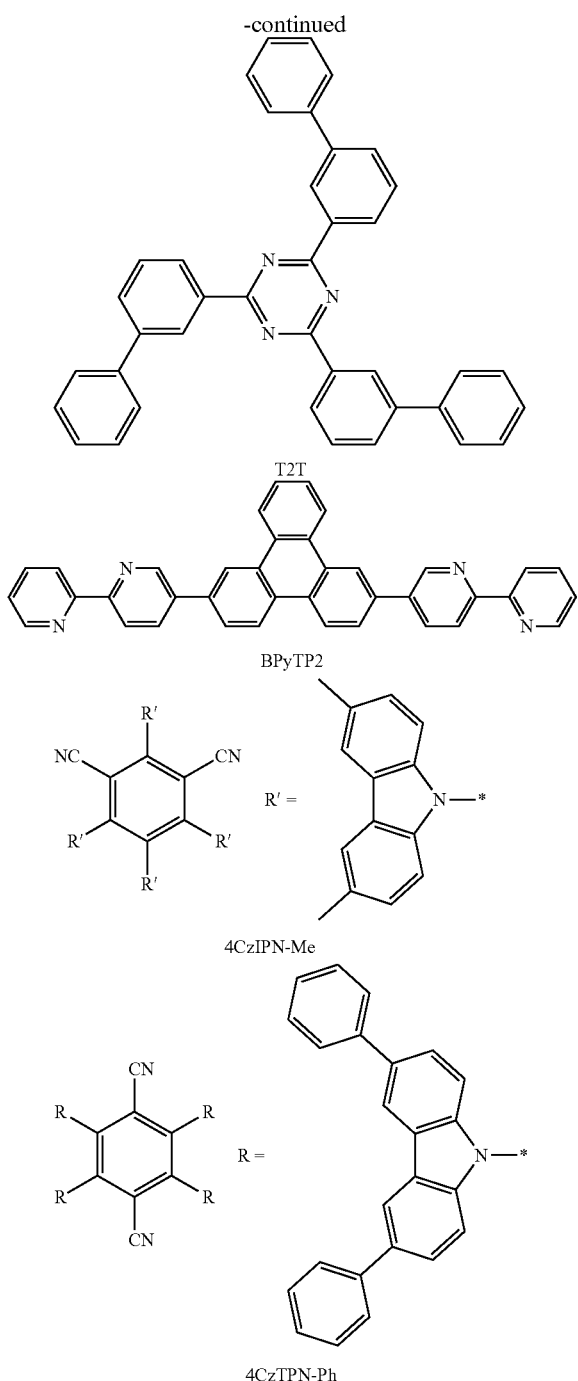

luminescent layer. In this example, the mass ratio of CBP:TPA-DCPP:TPA-ThQ was set at 75:24:1.0. Subsequently, a T2T layer was formed and a BPyTP2 layer was formed thereon. The total thickness (from HATCN to BpyTP2) of the organic layer was 120 nm. Furthermore, lithium fluoride (LiF) was vacuum deposited to a thickness of 0.8 nm, and aluminum (Al) was then deposited to a thickness of 100 nm to form a negative electrode, so that an organic EL element was obtained.

Comparative Example 1

An organic EL element was obtained in the same manner as in Example 1, except that 4CzIPN-Me was used as the delayed fluorescent material instead of TPA-DCPP.

Comparative Example 2

An organic EL element was obtained in the same manner as in Example 1, except that 4CzTPN-Ph was used as the delayed fluorescent material instead of TPA-DCPP.

<Evaluation 1>

The materials used in Examples and Comparative Examples were evaluated by the methods shown below. The results are shown in Table 1.

(Measurement of HOMO Level)

On an As-doped n-type bare Si wafer having a mirror-finished surface, a resistivity of 0.0030 to 0.0060 Ω·cm, and a crystal orientation <100>, a delayed fluorescent material or a luminescent material was deposited singly to a thickness of 100 nm respectively, and the HOMO level was measured by a photoelectron spectroscopic measurement apparatus AC-3E (manufactured by Riken Keiki Co., Ltd.) in the atmosphere.

(Measurement of LUMO Level and Measurement of Absorption Spectrum of Luminescent Material)

On a quartz substrate, a delayed fluorescent material or a luminescent material was deposited singly, and the absorption spectrum was measured by a UV-VIS-NIR spectrophotometer LAMBDA 950 (manufactured by Perkin Elmer, Inc.). In this example, the film thickness was adjusted such that the absorption peak at the longest wavelength side had an optical density (OD) of 0.1 to 1.0. With regard to the luminescent material, $P_{Abs}$ was defined as the maximal absorption value at the longest wavelength side.

With regard to the LUMO level, $\lambda_{edge}$ [nm] was defined as the wavelength at the intersection between the tangent line drawn along the trailing gradient on the long wavelength side of the longest wavelength-side peak of each of the obtained absorption spectra and the horizontal axis (wavelength axis), and the calculation was performed based on the formula 2 shown below, using the value of HOMO [eV] obtained by the method described above.

$$LUMO\ [eV] = HOMO + \left(\frac{1240}{\lambda_{edge}}\right) \quad \text{[Formula 2]}$$

The tangent line along the trailing gradient was drawn as follows. Moving along the spectral curve from the long wavelength side to the maximal value of an absorption peak, tangent lines may be drawn on the respective points on the spectral curve. The slope of the tangent lines increases as the curve rises (in other words, as the vertical axis increases). A tangent line drawn at the maximal value of the slope was Manufacturing of Organic EL Element Example 1

On a glass substrate having a positive electrode consisting of indium tin oxide (ITO) with a thickness of 110 nm, an organic layer described below was laminated by vacuum deposition. First, an HATCN layer was formed on the ITO, and a TAPC layer was then formed thereon. Subsequently, CBP (host material), TPA-DCPP (delayed fluorescent material) and TPA-ThQ (luminescent material) were co-deposited from different deposition sources so as to form a defined as the tangent line along the trailing gradient on the long wavelength side of the absorption spectrum.

(Measurement of Emission Spectrum of Delayed Fluorescent Material)

On a quartz substrate, a host material and a delayed fluorescent material were deposited such that the mass ratio therebetween was the same as the ratio in Examples or Comparative Examples, and the emission spectrum was measured by a fluorescence spectrophotometer FLUOROMAX (manufactured by Horiba, Ltd.). $P_{Em}$ was defined as the maximal value at the longest wavelength side of the spectrum obtained in the present measurement. As the conditions for the measurement, the slit width at the upstream or the downstream was 10 nm or less, and the film thickness was 30 nm or more and 200 nm or less.

TABLE 1

| | Luminescent material | Delayed fluorescent material | | |
|---|---|---|---|---|
| | TPA-ThQ | TPA-DCPP | 4CzIPN—Me | 4CzTPN—Ph |
| $P_{Abs}$ | 640 nm | — | — | — |
| $P_{Em}$ | — | 650 nm | 550 nm | 600 nm |
| ΔP | — | 10 nm | 90 nm | 40 nm |
| LUMO | 4.1 eV | 4.0 eV | 3.5 eV | 4.4 eV |
| ΔLUMO | — | 0.1 eV | 0.6 eV | −0.3 eV |
| HOMO | 5.7 eV | 5.9 eV | 5.9 eV | 6.3 eV |
| ΔHOMO | — | 0.2 eV | 0.2 eV | 0.6 eV |

<Evaluation 2>

The EL spectra, the voltage-current density characteristics, and the lowering ratio of chronological output to the initial output of organic EL elements obtained in Examples and Comparative Examples were measured. The EL spectra is shown in FIG. 2, the voltage-current density characteristics are shown in FIG. 3, and the lowering ratio of chronological output to the initial output is shown in FIG. 4, respectively.

Figure 2:
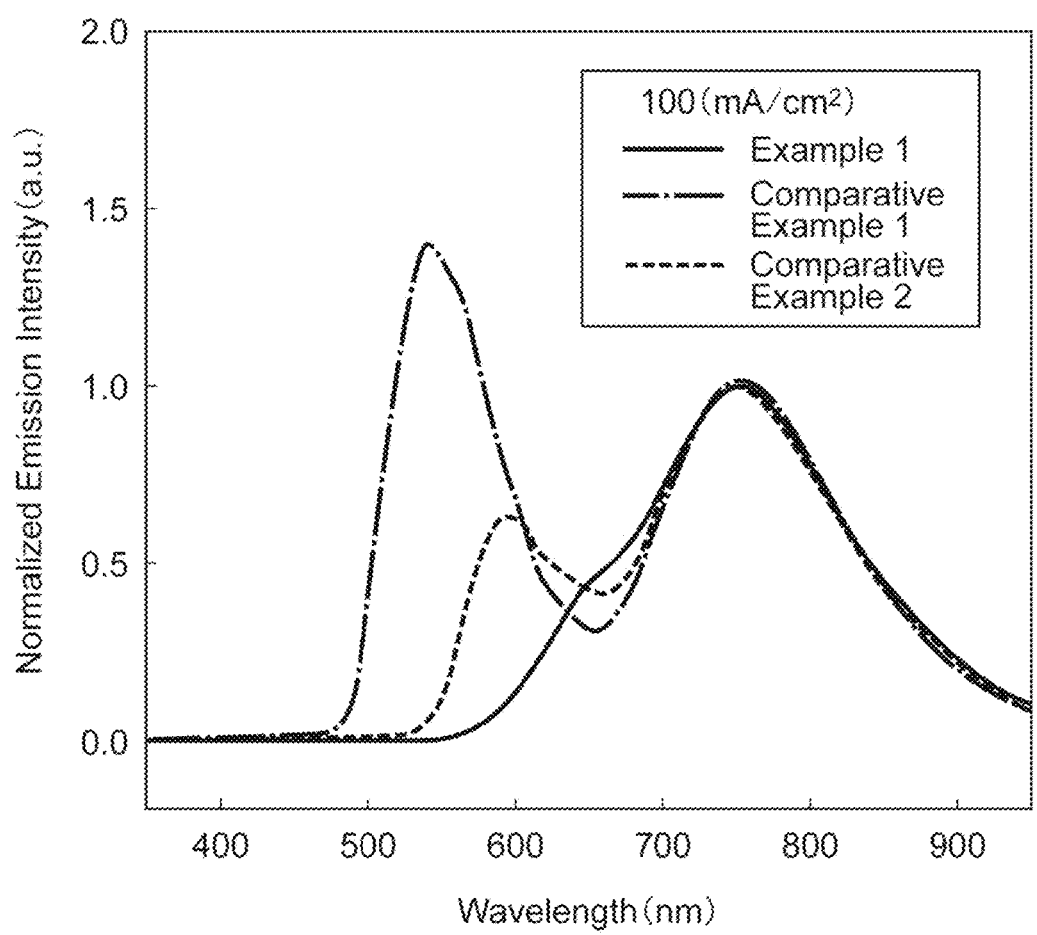
FIG. 2 is a chart showing the EL spectra of organic EL elements of Examples and Comparative Examples.

As clearly shown in FIG. 2, the organic EL element of Example 1 has a maximum luminescence in a near-infrared range of 700 nm or more (near a wavelength of 760 nm), without the presence of a maximum luminescence in the visible light range. On the other hand, each organic EL element in Comparative Examples 1 and 2 has a maximum luminescence in a near-infrared range of 700 nm or more (near a wavelength of 760 nm), and with the presence of a maximum luminescence derived from the delayed fluorescent material in the visible light range.

Figure 3:
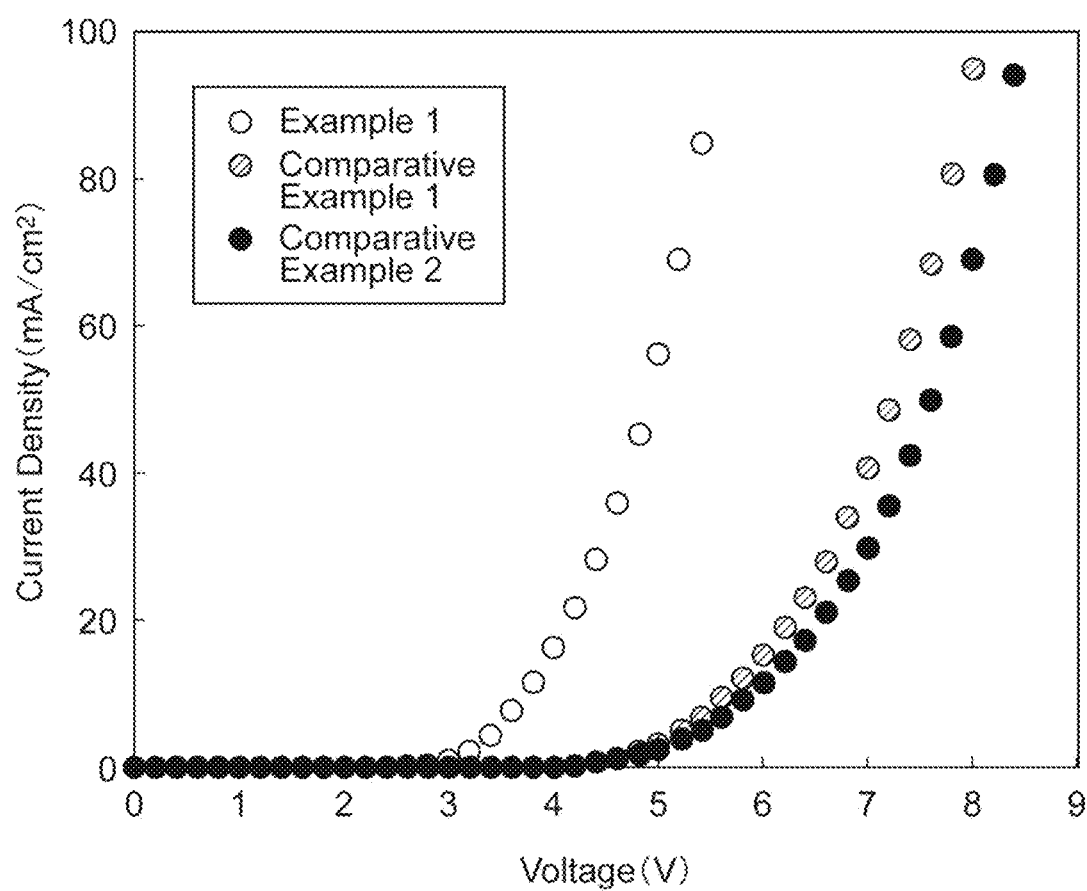
FIG. 3 is a chart showing the voltage-current density characteristics of organic EL elements of Examples and Comparative Examples.
Figure 4:
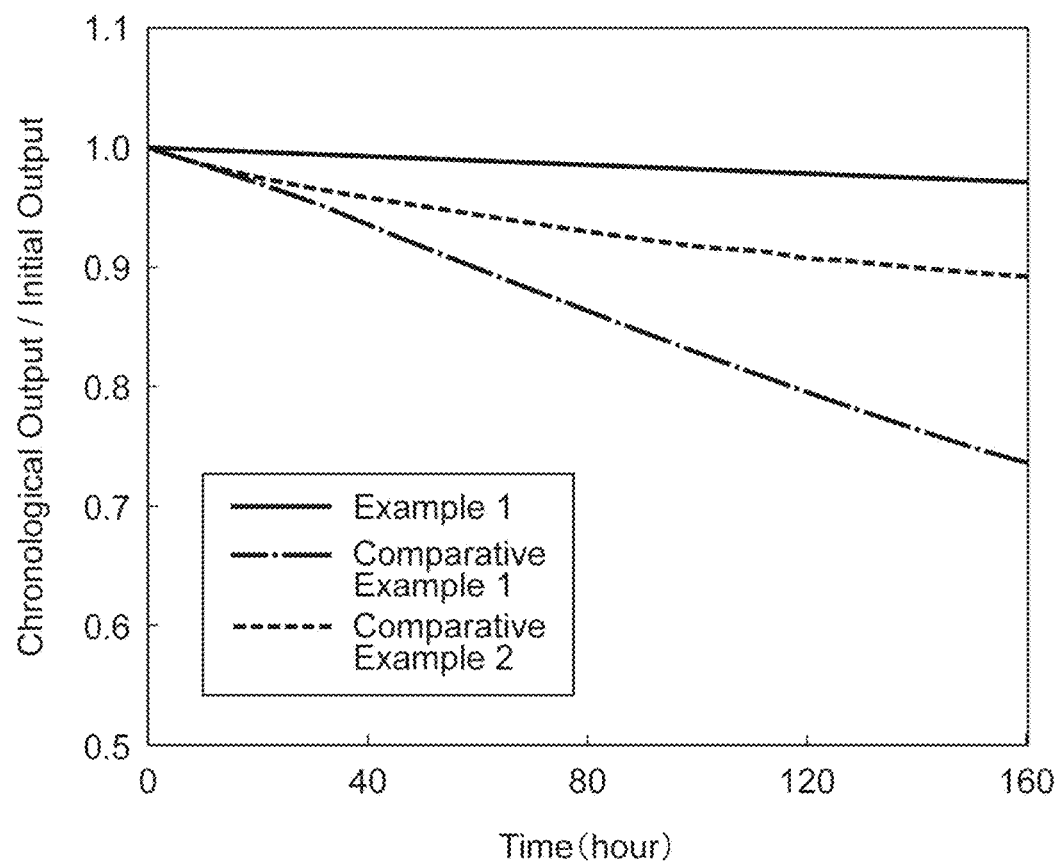
FIG. 4 is a chart showing the lowering rate of chronological output to the initial output of organic EL elements of Examples and Comparative Examples.

Also, as clearly shown in FIGS. 3 and 4, the organic EL element of Example 1 requires a smaller voltage to obtain the same level of luminance in comparison with the organic EL elements in Comparative Examples 1 and 2, which means that the organic EL element has excellent electric properties. Additionally, the organic EL element has a very small lowering ratio of chronological output to the initial output, which clearly means that the organic EL element has a long device life.

Figure 5:
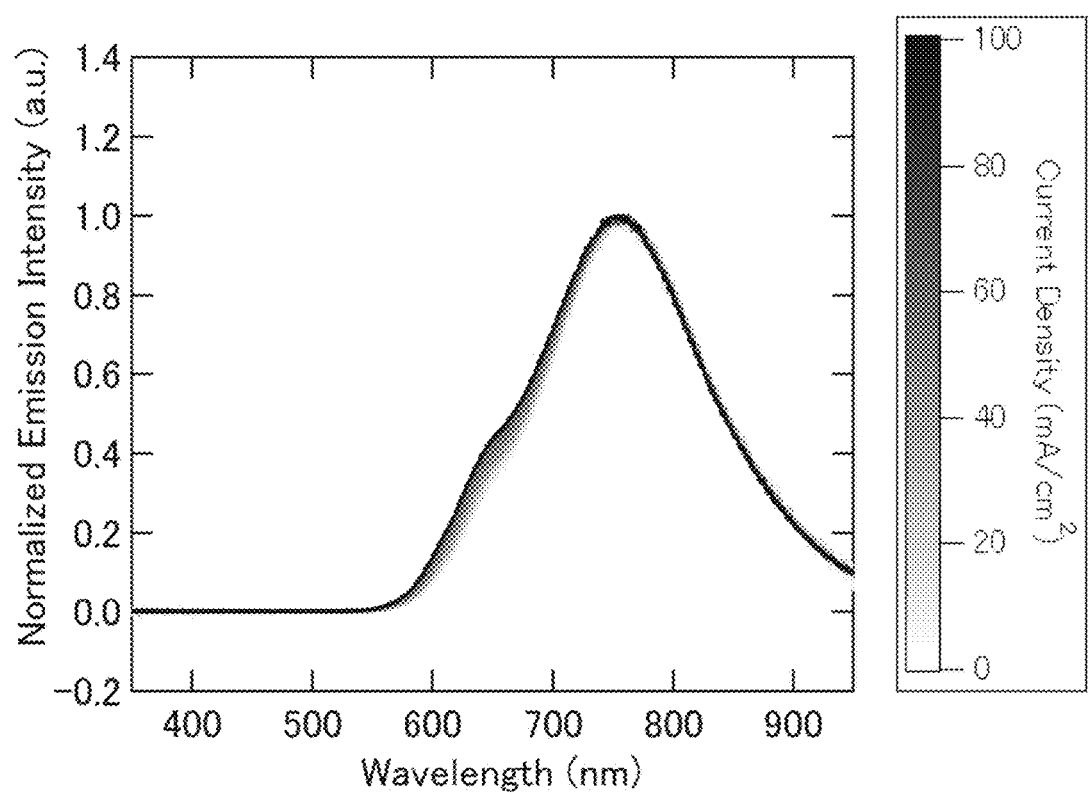
FIG. 5 is a chart showing the current density dependence of EL spectrum of an organic EL element of Example 1.
Figure 6:
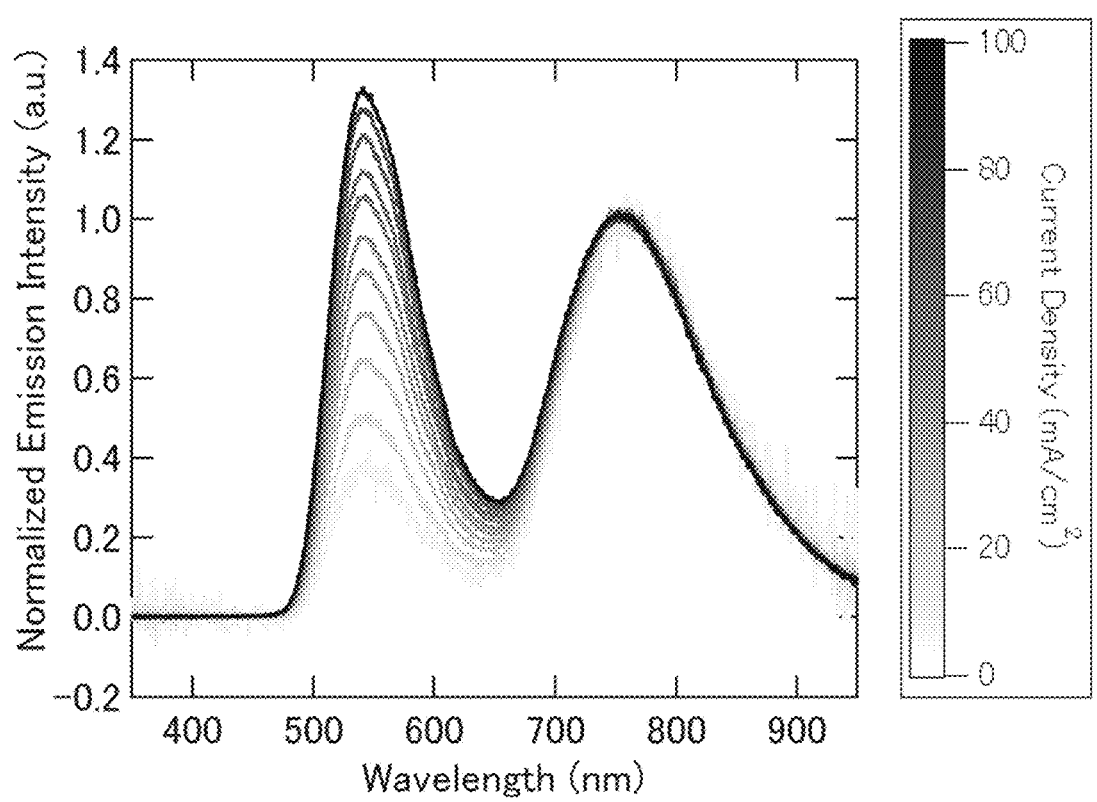
FIG. 6 is a chart showing the current density dependence of EL spectrum of an organic EL element of Comparative Example 1.
Figure 7:
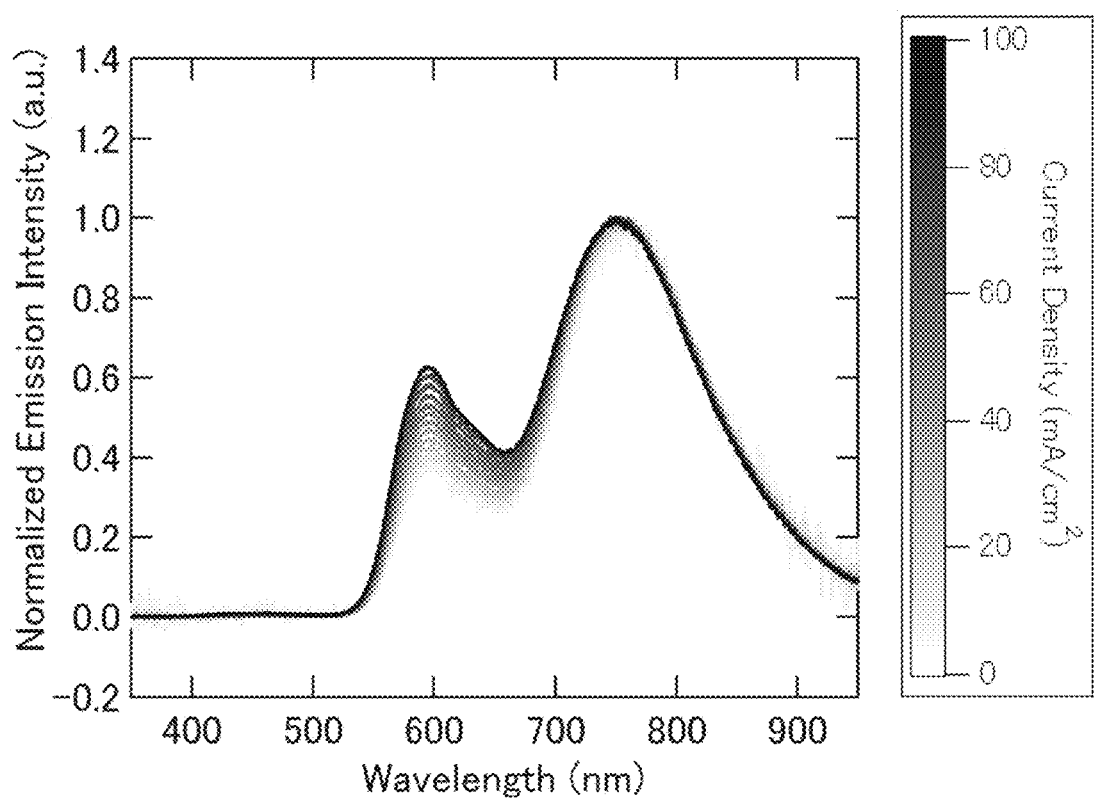
FIG. 7 is a chart showing the current density dependence of EL spectrum of an organic EL element of Comparative Example 2.

Furthermore, the current density dependence of EL spectra of the organic EL elements obtained in Examples and Comparative Examples were measured. The measurement results on the organic EL elements of Example 1, Comparative Example 1 and Comparative Example 2 are shown in FIGS. 5 to 7, respectively. As clearly shown in FIG. 6 and FIG. 7, the light emission in the visible light range of the organic EL elements in Comparative Examples 1 and 2 is intensified in the high current density region. On the other hand, as clearly shown in FIG. 5, no light emission of the organic EL element of Example 1 is observed in the visible light range even in the high current density region as a matter of course. When an organic EL element is used as the light source for bioinstrumentation, a high current density drive is assumed to be used due to the requirement for high output light. From this viewpoint also, it can be said that the organic EL element of Example 1 can be suitably used as the light source for bioinstrumentation.

The invention claimed is:

1. An organic electro-luminescent element having a luminescence peak in a near-infrared range, comprising a positive electrode, a negative electrode, and at least one organic layer including a luminescent layer located between the positive electrode and the negative electrode,
wherein the luminescent layer comprises a host material, a delayed fluorescent material, and a luminescent material, and
wherein the delayed fluorescent material and the luminescent material satisfy relationships (1) to (4) shown below:

$$\Delta HOMO + \Delta LUMO \leq 0.6 \text{ eV} \quad (1);$$

$$|\Delta HOMO| \leq 0.4 \text{ eV} \quad (2);$$

$$|\Delta LUMO| \leq 0.4 \text{ eV} \quad (3); \text{ and}$$

$$|P_{Abs} - P_{Em}| \leq 30 \text{ nm} \quad (4),$$

wherein "ΔHOMO" represents a value of a highest occupied molecular orbital (HOMO) energy level of the luminescent material minus a HOMO energy level of the delayed fluorescent material, wherein "ΔLUMO" represents a value of a lowest unoccupied molecular orbital (LUMO) energy level of the delayed fluorescent material minus a LUMO energy level of the luminescent material, wherein $P_{Abs}$ represents a maximal value at the longest wavelength side of an absorption spectrum of the luminescent material, and wherein $P_{Em}$ represents a maximal value at the longest wavelength side of an emission spectrum of the delayed fluorescent material.

2. The organic electro-luminescent element according to claim 1, wherein ΔHOMO+ΔLUMO in the relationship (1) is 0.5 eV or less.

3. The organic electro-luminescent element according to claim 1, wherein ΔHOMO+ΔLUMO in the relationship (1) is 0.4 eV or less.

4. The organic electro-luminescent element according to claim 1, wherein the absolute value of ΔHOMO in the relationship (2) is 0.3 eV or less.

5. The organic electro-luminescent element according to claim 1, wherein the absolute value of ΔLUMO in the relationship (3) is 0.3 eV or less.

6. The organic electro-luminescent element according to claim 1, wherein the absolute value of $P_{Abs}-P_{Em}$ in the relationship (4) is 25 nm or less.

7. The organic electro-luminescent element according to claim 1, wherein the absolute value of $P_{Abs}-P_{Em}$ in the relationship (4) is 20 nm or less.

8. The organic electro-luminescent element according to claim 1, wherein the absolute value of $P_{Abs}-P_{Em}$ in the relationship (4) is 0.15 nm or less.

9. The organic electro-luminescent element according to claim 1, wherein the luminescence peak appears in the near-infrared range including wavelengths between 700 nm and 800 nm.

10. The organic electro-luminescent element according to claim 1, wherein the luminescent layer comprises a smaller amount of the delayed fluorescent material as compared to an amount of the host material contained in the luminescent layer.

11. The organic electro-luminescent element according to claim 1, wherein the luminescent layer comprises a smaller amount of the luminescent material as compared to an amount of the host material contained in the luminescent layer.

12. The organic electro-luminescent element according to claim 1, wherein the luminescent layer comprises an amount of the host material that is 15 wt % to 99.9 wt % with respect to a total amount of the host material, the delayed fluorescent material and the luminescent material contained in the luminescent layer.

13. The organic electro-luminescent element according to claim 1, wherein the luminescent layer comprises an amount of the delayed fluorescent material that is 5.0 wt % to 50 wt % with respect to a total amount of the host material, the delayed fluorescent material and the luminescent material contained in the luminescent layer.

14. The organic electro-luminescent element according to claim 1, wherein the luminescent layer comprises an amount of the luminescent material that is 0.1 wt % to 5.0 wt % with respect to a total amount of the host material, the delayed fluorescent material and the luminescent material contained in the luminescent layer.

15. The organic electro-luminescent element according to claim 1, wherein the luminescent layer comprises an amount of the host material that is 50 wt % to 90 wt %, an amount of the delayed fluorescent material that is 5.0 wt % to 45 wt %, and an amount of the luminescent material that is 0.1 wt % to 5.0 wt %, with respect to a total amount of the host material, the delayed fluorescent material and the luminescent material contained in the luminescent layer.

16. A bioinstrumentation device comprising the organic electro-luminescent element according to claim 1 and a photo detector.

17. An organic electro-luminescent element having a luminescence peak in a near-infrared range, comprising a positive electrode, a negative electrode, and at least one organic layer including a luminescent layer located between the positive electrode and the negative electrode, wherein the luminescent layer comprises a host material, a delayed fluorescent material, and a luminescent material, and wherein the delayed fluorescent material and the luminescent material satisfy relationships (1) to (4) shown below:

$$\Delta HOMO + \Delta LUMO \leq 0.6 \text{ eV} \tag{1};$$

$$|\Delta HOMO| \leq 0.4 \text{ eV} \tag{2};$$

$$|\Delta LUMO| \leq 0.4 \text{ eV} \tag{3); and}$$

$$|P_{Abs} - P_{Em}| \leq 30 \text{ nm} \tag{4},$$

wherein "ΔHOMO" represents a value of a highest occupied molecular orbital (HOMO) energy level of the luminescent material minus a HOMO energy level of the delayed fluorescent material, wherein "ΔLUMO" represents a value of a lowest unoccupied molecular orbital (LUMO) energy level of the delayed fluorescent material minus a LUMO energy level of the luminescent material, wherein $P_{Abs}$ represents a maximal value at the longest wavelength side of an absorption spectrum of the luminescent material, and wherein $P_{Em}$ represents a maximal value at the longest wavelength side of an emission spectrum of the delayed fluorescent material.

18. The organic electro-luminescent element according to claim 17, wherein the host material comprises CBP, wherein the delayed fluorescent material comprises TPA-DCPP, and wherein the luminescent material comprises TPA-ThQ.

19. The organic electro-luminescent element according to claim 17, wherein the luminescent layer is formed at an approximate mass ratio of CBP:TPA-DCPP:TPA-ThQ=75:24:1.

20. A bioinstrumentation device comprising the organic electro-luminescent element according to claim 17 and a photo detector.

* * * * *

UNITED STATES PATENT AND TRADEMARK OFFICE
CERTIFICATE OF CORRECTION

PATENT NO. : 10,228,328 B2
APPLICATION NO. : 15/823599
DATED : March 12, 2019
INVENTOR(S) : Chihaya Adachi et al.

It is certified that error appears in the above-identified patent and that said Letters Patent is hereby corrected as shown below:

In the Claims

Column 37, Line 40, cancel the text beginning with "17. An organic electro-luminescent element" and ending "material." in Column 38, Line 29, and insert the following claim:
--17. An organic electro-luminescent element having a luminescence peak in a near-infrared range, comprising a positive electrode, a negative electrode, and at least one organic layer including a luminescent layer located between the positive electrode and the negative electrode,
wherein the luminescent layer comprises a host material, a delayed fluorescent material, and a luminescent material, and
wherein the delayed fluorescent material and the luminescent material satisfy relationships (1) to (4) shown below:
$\Delta HOMO + \Delta LUMO \leq 0.4$ eV... (1);
$|\Delta HOMO| \leq 0.3$ eV ... (2);
$|\Delta LUMO| \leq 0.3$ eV ... (3); and
$|P_{Abs} - P_{Em}| \leq 15$ nm ... (4),
wherein "$\Delta HOMO$" represents a value of a highest occupied molecular orbital (HOMO) energy level of the luminescent material minus a HOMO energy level of the delayed fluorescent material, wherein "$\Delta LUMO$" represents a value of a lowest unoccupied molecular orbital (LUMO) energy level of the delayed fluorescent material minus a LUMO energy level of the luminescent material, wherein $P_{Abs}$ represents a maximal value at the longest wavelength side of an absorption spectrum of the luminescent material, and wherein $P_{Em}$ represents a maximal value at the longest wavelength side of an emission spectrum of the delayed fluorescent material.--

Signed and Sealed this
Eighteenth Day of June, 2019

Andrei Iancu
*Director of the United States Patent and Trademark Office*